United States Patent
Trollsas et al.

(10) Patent No.: US 12,090,136 B2
(45) Date of Patent: *Sep. 17, 2024

(54) APPARATUS FOR TREATING BENIGN PROSTATIC HYPERPLASIA

(71) Applicant: RESURGE THERAPEUTICS, INC., San Jose, CA (US)

(72) Inventors: Olof Mikael Trollsas, San Jose, CA (US); John J. Stankus, Santa Cruz, CA (US); Shahram Shawn Gholami, Monte Sereno, CA (US)

(73) Assignee: Resurge Therapeutics, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/528,691

(22) Filed: Dec. 4, 2023

(65) Prior Publication Data

US 2024/0115544 A1 Apr. 11, 2024

Related U.S. Application Data

(63) Continuation of application No. 18/062,436, filed on Dec. 6, 2022, now Pat. No. 11,957,654, which is a continuation of application No. 17/727,675, filed on Apr. 22, 2022, now Pat. No. 11,602,516.

(60) Provisional application No. 63/304,599, filed on Jan. 29, 2022.

(51) Int. Cl.
 *A61K 31/337* (2006.01)
 *A61K 45/06* (2006.01)
 *A61P 35/00* (2006.01)

(52) U.S. Cl.
 CPC ............ *A61K 31/337* (2013.01); *A61K 45/06* (2013.01); *A61P 35/00* (2018.01)

(58) Field of Classification Search
 None
 See application file for complete search history.

(56) References Cited

U.S. PATENT DOCUMENTS

| | | |
|---|---|---|
| 5,116,615 A | 5/1992 | Gokcen et al. |
| 5,595,985 A | 1/1997 | Labrie |
| 5,945,115 A | 8/1999 | Dunn et al. |
| 6,177,404 B1 | 1/2001 | DeFeo-Jones et al. |
| 6,277,391 B1 | 8/2001 | Seo et al. |
| 6,689,803 B2 | 2/2004 | Hunter |
| 6,759,431 B2 | 7/2004 | Hunter |
| 7,008,633 B2 | 3/2006 | Yang et al. |
| 7,015,253 B2 | 3/2006 | Escandon et al. |
| 7,906,136 B2 | 3/2011 | Wong et al. |
| 8,002,745 B2 | 8/2011 | Kaal et al. |
| 8,133,491 B1 | 3/2012 | Selman et al. |
| 8,313,763 B2 | 11/2012 | Margaron et al. |
| 8,362,086 B2 | 1/2013 | Soll et al. |
| 8,900,252 B2 | 12/2014 | Lamson et al. |
| 9,186,464 B2 | 11/2015 | Franklin |
| 9,545,464 B2 | 1/2017 | Roche et al. |
| 9,814,685 B2 | 11/2017 | Baltezor et al. |
| 10,004,813 B2 | 6/2018 | Hochberg et al. |
| 10,159,683 B2 | 12/2018 | Wong et al. |
| 10,265,477 B2 | 4/2019 | Schwab et al. |
| 10,639,273 B2 | 5/2020 | Puri et al. |
| 10,668,188 B2 | 6/2020 | Wang |
| 10,792,427 B2 | 10/2020 | Metzner et al. |
| 11,013,731 B2 | 5/2021 | Kundu et al. |
| 11,097,061 B2 | 8/2021 | Gerlett |
| 11,110,067 B2 | 9/2021 | Sharp et al. |
| 2002/0055666 A1 | 5/2002 | Hunter et al. |
| 2004/0002647 A1 | 1/2004 | Desai |
| 2005/0064045 A1 | 3/2005 | Zhong et al. |
| 2006/0063732 A1 | 3/2006 | Vogel et al. |
| 2006/0217680 A1 | 9/2006 | Barath |
| 2007/0042046 A1 | 2/2007 | Saffie et al. |
| 2007/0280992 A1 | 12/2007 | Margaron et al. |
| 2008/0194663 A1 | 8/2008 | Dunn |
| 2008/0286205 A1 | 11/2008 | Lennernas et al. |
| 2008/0317736 A1 | 12/2008 | Franano |
| 2009/0227633 A1 | 9/2009 | Damaj |
| 2009/0248034 A1 | 10/2009 | Dolan et al. |
| 2010/0081681 A1 | 4/2010 | Blagosklonny |
| 2013/0197446 A1 | 8/2013 | Gustafsson et al. |

(Continued)

FOREIGN PATENT DOCUMENTS

| | | |
|---|---|---|
| CN | 100431631 C | 11/2008 |
| EP | 1845942 B1 | 4/2014 |

(Continued)

OTHER PUBLICATIONS

Li, Jun, et al. "Synaptic P-Rex1 signaling regulates hippocampal long-term depression and autism-like social behavior." Proceedings of the National Academy of Sciences 112.50 (2015): E6964-E6972.*

Li, Shidong, et al. "Dosimetric and technical considerations for interstitial adenoviral gene therapy as applied to prostate cancer." International Journal of Radiation Oncology* Biology* Physics 55.1 (2003): 204-214.*

Melo, Gustavo Barreto, et al. "Critical analysis of techniques and materials used in devices, syringes, and needles used for intravitreal injections." Progress in Retinal and Eye Research 80 (2021): 100862.*

(Continued)

*Primary Examiner* — Patrick T Lewis
(74) *Attorney, Agent, or Firm* — SQUIRE PATTON BOGGS (US)

(57) ABSTRACT

Minimally invasive treatment methods for benign prostatic hyperplasia (BPH) tissue. A system includes a sustained release formulation comprising a cytostatic or cytotoxic drug, and an applicator or delivery system for local delivery of a composition comprising or consisting essentially of the sustained release formulation to the prostate. The applicator containing the composition is characterized by a KIR value of between 40 and 400 Centipoise per unit area.

20 Claims, 11 Drawing Sheets

(56) References Cited

U.S. PATENT DOCUMENTS

| | | |
|---|---|---|
| 2013/0325143 A1 | 12/2013 | Lamson et al. |
| 2014/0350516 A1 | 11/2014 | Schwab et al. |
| 2015/0094667 A1 | 4/2015 | Verhoeven et al. |
| 2015/0273117 A1 | 10/2015 | Wang |
| 2015/0322064 A1 | 11/2015 | Ren et al. |
| 2016/0024099 A1 | 1/2016 | Ren et al. |
| 2020/0101012 A1 | 4/2020 | Klein et al. |
| 2020/0113820 A1 | 4/2020 | Pui et al. |
| 2020/0170992 A1 | 6/2020 | Dizerega et al. |
| 2022/0387731 A1 | 12/2022 | Diaz et al. |

FOREIGN PATENT DOCUMENTS

| | | |
|---|---|---|
| WO | WO 2009/060473 A2 | 5/2009 |
| WO | WO 2016/013829 A1 | 1/2016 |
| WO | WO 2018/128173 A1 | 7/2018 |
| WO | WO 2021/050953 A1 | 3/2021 |
| WO | WO 2022/067309 A1 | 3/2022 |
| WO | WO 2023/147080 A1 | 8/2023 |

OTHER PUBLICATIONS

Invitation To Pay Additional Fees And, Where Applicable, Protest Fee of the PCT/US2023/011776 mailed Apr. 21, 2023; 14 pages.

International search report and written opinion of PCT/US2023/011776 mailed Jun. 13, 2023; 19 pages.

Final office action of the U.S. Appl. No. 17/727,680 mailed Dec. 19, 2022; 13 pages.

Non-final Office Action mailed Oct. 27, 2022 for U.S. Appl. No. 17/092,079.

Non-Final Office action mailed Jul. 27, 2023 for U.S. Appl. No. 17/727,680; 17 pages.

U.S. Appl. No. 17/727,680 Non-Final Office Action mailed Aug. 25, 2022. 14 pages.

Ahmed, "Approaches to develop PGLA based in situ gelling system with low initial burst", Pak. J. Pharm. Sci., Mar. 2015, vol. 28, No. 2, pp. 657-665.

Belz, Jodi Elizabeth, "Smart brachytherapy spacers for combined chemo-radiation therapy: local delivery of nanoparticles, chemotherapeutics, and molecular inhibitors for cancer treatment", Diss. Northeastern University Boston, May 2017, 188 pages.

Bode et al., "Paclitaxel encapsulated in cationicliposomes: a new option for neovascular targeting for the treatment of prostate cancer", Oncol Rep. Aug. 2009, 22 (2):321-6. PMID: 19578772.

Brady et al (A pilot study in intraparenchymal therapy delivery in the prostate: a comparison of delivery with a porous needle vs. standard needle. BMC Urology (2018) 18:66) (Year: 2018). https://doi.org/10.1186/s12894-018-0378-8. 8 pages.

Cancaster—https://www.vitalitymedical.com/blog/selecting-syringes-and-needles.html; 2015.

Cilurzo et al., "Injectability Evaluation: An Open Issue", AAPS PharmSciTech, vol. 12, No. 2, Jun. 2011, pp. 604-609; DOI: 10.1208/s12249-011-9625-y.

De Bono JS et al. Gupta 8, Sartor AO; Tropic Investigators. Prednisone plus cabazitaxel or mitoxantrone for metastatic castration-resistant prostate cancer progressing after docetaxel treatment: a randomised open-label trial. Lancet. Oct. 2, 2010;376(9747):1147-54. doi: 10.1016/S0140-6736(10)61389-X. PMID: 20888992.

Dhingra N. and Bhagwat D., "Benign prostatic hyperplasia: An overview of existing treatment.", Indian J Pharmacol. Feb. 2011; 43(1):6-12; doi: 10.4103/0253-7613.75657. PMID: 21455413; PMCID: PMC3062123.

Jackson et al., "The Suppression of Human Prostate Tumor Growth in Mice by the Intratumoral Injection of a Slow-Release Polymeric Paste Formulation of Paclitaxel", Cancer Research 60, pp. 4146-4151, Aug. 1, 2000.

Koshkin et al., "Randomized phase II trial of neoadjuvant evero.limus in patients with high-risk localized prostate Cancer", Investigational New Drugs 37, 2019, pp. 559-566; doi: 10.1007/s10637-019-00778-4.

Le Broc et al (Development of innovative paclitaxel-loaded PLGA nanoparticles: Study of their antiproliferative activity and their molecular interactions on prostatic cancer cells. International Journal of Pharmaceutics 454, 2013, pp. 712-719.

Lesovaya, et al., "Rapatar, a nanoformulation of raparnycin, decreases chemicallyinduced benign prostate hyperplasia in rats", Oncotarget, 2015, vol. 6, No. 12, pp. 9718-9727.

Liu et al., "Roles of autophagy in androgen-induced benign prostatic hyperplasia in castrated rats", Experimental and Therapeutic Medicine, 2018, 15: 2703-2710.

Lu et al., "Raparnycin-induced autophagy attenuates hormone-imbalance-induced chronic non-bacterial prostatitis in rats via the inhibition of NLRP3 inflammasome-rnediateci inflammation", Molecular Medicine Reports 19, 2019, pp. 221-230.

Pal et al., "Critical appraisal of cabazitaxel in the management of advanced prostate cancer", Clinical Interventions in Aging, 2010, vol. 5, pp. 395-402; doi: 10.2147/CIA.S14570.

Sartor, "Eligard® 6: A New Form of Treatment for Prostate Cancer", European Urology Supplements 5, 2006, pp. 905-910.

Shikanov et al. "Intratumoral Delivery of Paclitaxel for Treatment of Orthotopic Prostate Cancer", Journal Of Pharmaceutical Sciences, vol. 98, No. 3, Mar. 1, 2009, pp. 1005-1014, XP055509946.

Watt et al., "Injectability as a function of viscosity and dosing materials for subcutaneous administration", International Journal of Pharmaceutics, vol. 554, 2019, pp. 376-386.

Yared et al., "Update on taxane development: new analogs and new formulations", Drug Design Development and Therapy, 2012, vol. 6, pp. 371-384. doi: 10.2147/DDDT.528997.

Application of Otto, U.S. Court of Customs and Patent Appeals, , Feb. 13, 1963, 50 C.C.P.A. 938, 312 F.2d 937, 33 pages.

Application of Casey, U.S. Court of Customs and Patent Appeals, Jan. 12, 1967, 54 C.C.P.A. 938, 370 F.2d 576, 37 pages.

*In re Young*, United States Court of Customs and Patent Appeals. | Mar. 25, 1935 | 22 C.C.P.A. 1060, 75 F.2d 996, 25 USPQ 69 (CCPA 1935).

Ex Parte Gerald J. Bruck and Ahmed Kamel, PTTAB, Appeal 2017-010719, U.S. Appl. No. 14/071,774, filed Jul. 30, 2018, 11 pages.

*Celltrion, Inc.* v. *Chugai Seiyaku Kabushiki Kaisha, Genetech, Inc.*, PTTAB, IPR2022-00579, U.S. Pat. No. 10,874,677 B2, Aug. 29, 2023, 29 pages.

\* cited by examiner

FIG. 3A

| TABLE 3 | | | | |
|---|---|---|---|---|
| Unit Volume (ml) | Viscosity (cP) | Needle Length (cm) | Needle ID (cm) | KIR (cP/cm$^2$) |
| 0.5 | 300 | 15 | 0.06 | 2 |
| 0.5 | 500 | 15 | 0.06 | 4 |
| 0.5 | 300 | 20 | 0.06 | 4 |
| 0.25 | 300 | 15 | 0.06 | 5 |
| 0.5 | 500 | 20 | 0.06 | 7 |
| 0.25 | 500 | 15 | 0.06 | 8 |
| 0.25 | 300 | 20 | 0.06 | 8 |
| 0.1 | 267 | 15 | 0.06 | 10 |
| 0.1 | 300 | 15 | 0.06 | 11 |
| 0.25 | 500 | 20 | 0.06 | 13 |
| 0.1 | 500 | 15 | 0.06 | 19 |
| 0.5 | 2500 | 15 | 0.06 | 19 |
| 0.1 | 533 | 15 | 0.06 | 20 |
| 0.1 | 300 | 20 | 0.06 | 20 |
| 0.1 | 500 | 20 | 0.06 | 33 |
| 0.5 | 2500 | 20 | 0.06 | 33 |
| 0.25 | 2500 | 15 | 0.06 | 38 |
| 0.5 | 5000 | 15 | 0.06 | 38 |
| 0.1 | 1065 | 15 | 0.06 | 40 |
| 0.25 | 2500 | 20 | 0.06 | 67 |
| 0.5 | 5000 | 20 | 0.06 | 67 |
| 0.25 | 5000 | 15 | 0.06 | 75 |
| 0.5 | 10000 | 15 | 0.06 | 75 |
| 0.1 | 2500 | 15 | 0.06 | 94 |
| 0.25 | 5000 | 20 | 0.06 | 133 |
| 0.5 | 10000 | 20 | 0.06 | 133 |
| 0.25 | 10000 | 15 | 0.06 | 150 |

FIG. 3B

| TABLE 3 (cont.) | | | | |
|---|---|---|---|---|
| Unit Volume (ml) | Viscosity (cP) | Needle Length (cm) | Needle ID (cm) | KIR (cP/cm$^2$) |
| 0.1 | 2500 | 20 | 0.06 | 167 |
| 0.1 | 5000 | 15 | 0.06 | 188 |
| 0.25 | 10000 | 20 | 0.06 | 267 |
| 0.05 | 3000 | 20 | 0.08 | 300 |
| 0.05 | 2500 | 20 | 0.06 | 333 |
| 0.1 | 5000 | 20 | 0.06 | 333 |
| 0.1 | 10000 | 15 | 0.06 | 375 |
| 0.05 | 4000 | 20 | 0.08 | 400 |
| 0.05 | 5000 | 20 | 0.06 | 667 |
| 0.1 | 10000 | 20 | 0.06 | 667 |
| 0.05 | 10000 | 20 | 0.08 | 1,000 |
| 0.05 | 10000 | 20 | 0.06 | 1,333 |

APPARATUS FOR TREATING BENIGN PROSTATIC HYPERPLASIA

FIELD

Minimally invasive, local treatments for men's health and, more particularly, lower urinary tract symptoms.

BACKGROUND

Benign Prostatic Hyperplasia (BPH) is a noncancerous increase in size of the prostate gland due to proliferation of glandular epithelial tissue, smooth muscle and connective tissue within the prostate transition zone that causes lower urinary tract symptoms. Lower urinary tract symptoms (LUTS) include voiding or obstructive symptoms such as hesitancy, poor and/or intermittent stream, straining, feeling of incomplete bladder emptying, and storage or irritative symptoms such as frequency, urgency, urge incontinence, and nocturia. It affects approximately half of men aged 50 and over and by age 80, 90% of men are affected. Treatment options consist of lifestyle changes, medications, various procedures, and surgery. Lifestyle changes consist of weight loss, exercise, and decreased caffeine consumption. With more significant symptoms, oral medications such as alpha blockers (e.g., terazosin) or 5-alpha-reductase inhibitors (e.g., finasteride) are prescribed. These medications, requiring daily dosing for patient compliance, may require a long onset to show efficacy, if at all, and carry side effects such as ejaculation changes, erectile dysfunction, weakness, headaches, and decreased libido.

There is an unmet clinical need to treat BPH with improved and sustained efficacy, administered via a less invasive procedure and with less associated side effects.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A and 3B provide examples of K-Injectate Ratings (KIRs).

DETAILED DESCRIPTION

Figure 1:
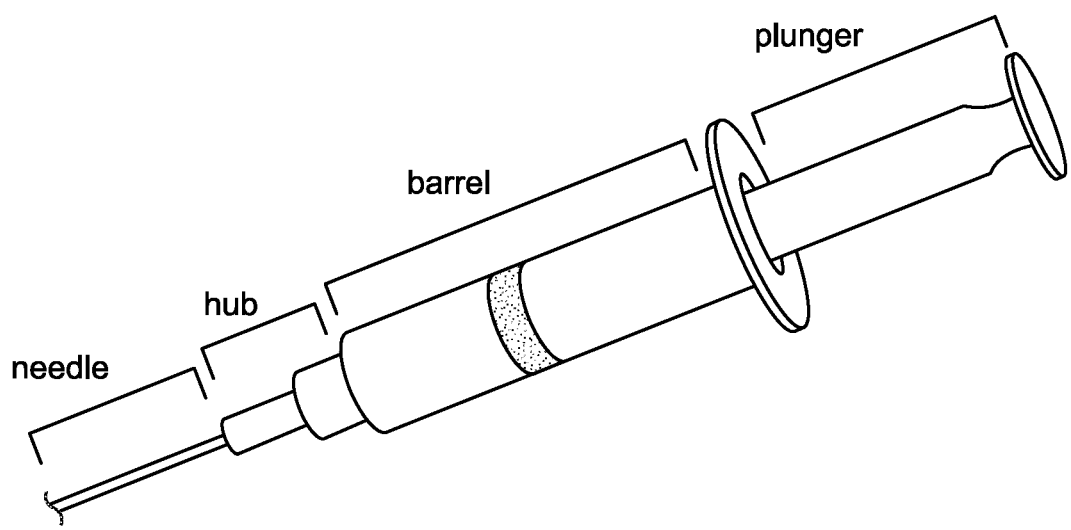
FIG. 1 is a PRIOR ART perspective view of a needle syringe.

The disclosure is generally directed to achieving a local delivery of a sustained release formulation at a specification for efficacious treatment of a target tissue associated with the prostate, and/or providing relief of urinary tract symptoms originating from or associated with an enlarged prostate while mitigating if not avoiding damage to nearby prostate structures or the urethra. The treatment may be used by itself, or in combination with other known treatments.

In view of the foregoing, disclosed herein is a method for delivery of a sustained release formulation (SRF) in an efficacious manner and with less side effects to a patient. The method uses an apparatus comprising a needle syringe containing a composition, which comprises the SRF (hereinafter "composition" will refer to a composition that comprises the SRF, unless specifically noted otherwise). The method includes dispensing one or more unit volumes of composition from the needle syringe at a respective one or more target tissue locations of the prostate. The apparatus is characterized by its K-injectate Rating (KIR) defined by the following relationship:

$$KIR = \frac{\mu L^2}{vD}(10^{-6})$$

Where $\mu$ is the absolute viscosity (cP) of the composition, L is the needle length (cm) measured from the needle tip to the end of the needle hub, D is the needle lumen diameter (cm), and v is a unit volume (cm$^3$ or cc) of the composition contained in the syringe barrel. Each unit volume represents a maximum volume of the composition dispensed at a single location of the target tissue. In some embodiments the syringe holds a plurality of unit volumes, which enables the dispensing of a unit volume at each of a corresponding plurality of discrete locations of the target tissue.

There is also disclosed an apparatus for prostate treatment. The apparatus comprises a needle syringe and the composition contained within the syringe. The apparatus is adapted to deliver the composition in one or more unit volume increments to a target tissue, as defined by its KIR value.

KIR values for the method, apparatus, medical device, and system according to the disclosure may range from between 10 and 1000, 10 and 300, or 40 and 400. The units of KIR are centipoise per unit area.

Prostate treatment according to the disclosure may be described as a prostate treatment having three characteristics: minimal uncontrolled drug diffusion (e.g., as shown in Table 8), sustained release and efficacy, and a unit volume as defined herein. The KIR identifies the needle syringe capable of delivering these one or more unit volumes of a composition, in a safe, repeatable pattern by a health professional and without imposing significant compromises on the composition's ability to achieve minimal uncontrolled drug diffusion, sustained release and efficacy.

Accordingly, in one aspect, a treatment of prostatic hyperplasia tissue, as provided herein, includes the delivery of a drug or multiple drugs to the tissue in a sustained release manner using a needle syringe containing the SRF. The treatment may be used with, or in addition to treatments involving removal/ablation of tissue, and/or delivery of energy to the tissue and additionally the administering of various agents. Methods according to the disclosure may additionally, or alternatively, be administered after a treatment of BPH according to other methods.

Access to prostatic tissue may be achieved in a transurethral, transrectal or transperineal manner via an existing body orifice. It may be beneficial and less invasive to access the tissue by either transrectal or transperineal approaches. The advantages with a transrectal or transperineal approach include one or more (1) oral and/or local anesthesia application instead of general anesthesia, (2) less trauma to the urethra tract and less resulting side effects also reducing the need for catheterization, (3) faster recovery time for the patient, (4) familiar treatment for the urologist physician similar to prostate cancer biopsy. For access by transrectal or transperineal approach, guidance may be provided by ultrasound, x-ray, computed tomography, magnetic resonance imaging or other imaging modality. Ultrasound imaging may be beneficial given that ultrasound is utilized for prostate biopsy. The transrectal approach closely mirrors the present prostate ultrasound and biopsy techniques familiar to urologists. Transrectal and transperineal approaches both avoid interaction with the urethra, which limits the caustic effects of urethral procedures therefore minimizing side effects and dysuria associated with currently available BPH procedures.

The drug portion of the composition may be an anti-inflammatory, anti-proliferative, cytoreductive, cytostatic, and/or cytotoxic drug that would affect the prostate size and gland proliferation. The apparatus enables delivery of one or more drugs into the target tissue. Once delivered to the target tissue, the drug may then release from the SRF in a slow, sustained release fashion, optionally delivered as an initial burst of the drug, followed by a slow, sustained release of the drug to the target release. The amount or lack of burst and/or the "slow, sustained release" release period may depend on the drug delivered to the prostate, the SRF properties, and the KIR value, as will be appreciated in view of this disclosure. In some embodiments a slow, sustained release may occur over, e.g., a 24-hour period, 3-7 days, 1-4 weeks, 1 to 12 months, 3 months, or 6 months.

In another aspect there is a system for treating BPH including a needle syringe, the sustained release formulation (SRF), and imaging device for locating a target tissue of the prostate. The imaging device, e.g., ultrasound, may be used both as a needle guide to the target tissue and for sizing the prostate. Once the prostate size is determined, the number, n, of unit volumes, v, for injection may be determined. A needle syringe according to the disclosure may hold one or a plurality of unit volumes dispensable from the needle to treat the prostate in a controlled manner, as determined by the KIR value for the syringe containing the composition. The KIR value is between 10 and 1000, 10 and 300, or 40 and 400.

In another aspect there is a method for making a medical device for treating the prostate, including the steps of combining at least one drug with at least one polymer carrier to form a composition comprising an SRF, wherein the composition is contained within a needle syringe, and wherein the needle syringe containing the composition has a KIR value of between 10 and 1000, 10 and 300, or 40 and 400.

Treatment of BPH by a needle injection, in a small quantity (unit volume) at a plurality of locations in the target tissue, offers several benefits over other methods. Among the benefits are less invasive procedures leading to greater patient acceptance and less complications during patient treatment, less frequent procedures needed, and reduced incidence of drug affecting nearby tissue leading to such outcomes as adverse consequences for urinary or sexual function.

For purposes of this disclosure, the following terms and definitions apply:

The following are examples of the polymer naming nomenclature appearing in the listing of additional disclosed embodiments following the detailed description. Other examples not explicitly spelled out here use the same rationale: PLGA8515A (0.3 dl/g) means poly(lactide-co-glycolide) with a monomer ratio of 85/15, end capped with an acid group (A), and an inherent viscosity of 0.3 dl/g; and PLGA6535E (0.5 dl/g) means poly(lactide-co-glycolide) with a monomer ratio of 65/35, end capped with an ester groups (E), and an inherent viscosity of 0.5 dl/g; and PLGA5050A (0.2 dl/g) means poly(lactide-co-glycolide) with a monomer ratio of 50/50, end capped with an acid group (E), and an inherent viscosity of 0.2 dl/g; and Poly (lactide-co-glycolide) is typically poly(D,L-lactide-co-glycolide) but could also be e.g. any or a mixture of poly(D, L-lactide-co-glycolide), poly(D-lactide-co-glycolide), and poly(L-lactide-co-glycolide).

The terms "about" or "approximately" is defined herein as 30%, 20%, 15%, 10% 5% 4% 3% 2%1.5%, 1%, between 1-2%, 1-3%, 1-5% or 0.5%-5% less or more than, less than, or more than a stated value, a range or each endpoint of a stated range, or a one-sigma, two-sigma, three-sigma variation from a stated mean or expected value (Gaussian distribution). For example, dl is about d2 means dl is 30% 20% 15% 10% 5% 4% 3% 2% 1.5% 1%, 0% or between 1-2%, 1-3%, 1-5%, or 0.5%-5% different from d2. If dl is a mean value, then d2 is about dl means d2 is within a one-sigma, two-sigma, or three-sigma variance from dl. It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately."

The term "drug" or "agent" as used herein is defined as a therapeutic substance, other than food, used in the prevention, diagnosis, alleviation, treatment, or cure of disease. Unless stated otherwise, "drug" and "agent" shall have the same meaning.

The term "cytostatic" as used herein refers to a drug that is non-toxic to cells but does mitigate cell proliferation and permit cell migration. Cytostatic drugs may include without limitation rapamycin, sirolimus, everolimus, zotarolimus, myolimus, temsirolimus, tacrolimus, macrolide antibiotics, ridaforolimus, biolimus, novolimus, deforolimus, structural derivatives and functional analogues of rapamycin and any macrolide immunosuppressive drug. mTOR/PI3K dual inhibitors may also be utilized including dactolisib, BGT226, SF1126, PKI-587, and NVPBE235, mTORC1/mTORC2 dual inhibitors may also be utilized including sapanisertib, AZD8055, AZD2014 as derived from morpholino pyrazolopyrimidine.

The term "cytotoxic" as used herein refers to a drug that inhibits cell growth and proliferation such as chemotherapeutics. These drugs may include but are not limited to paclitaxel, taxanes, protaxel, vincristine, etoposide, nocodazole, indirubin, anthracycline derivatives, daunorubicin, daunomycin, tauromustine, bofumustane, carboplatin, carmustine, cisplatin, docetaxel, gemcitabine, mitomycin, procarbazine, and plicamycin. These drugs may also be apoptotic such as TGF, topoisomerase inhibitors, including, 10-hydroxycamptothecin, irinotecan, and doxorubicin.

The term "composition" as used herein means a product of mixing or combining various elements or ingredients. Whenever the word "composition" is used, it will be understood that the composition comprises an SRF. The term "polymer composition" however is not a composition that comprises the SRF.

The term "absolute viscosity" as used herein means the viscosity measured relative to the viscosity of a known substance. Unless stated otherwise "absolute viscosity" (as compared to inherent viscosity) is represented by the symbol $\mu$. Absolute viscosities may be measured using a calibrated digital rotational viscometer spindle (no. 1 size) with 10 mL solutions in 40 ml polypropylene vials with an approximately 50% submerged spindle solution contact, with measurements made at room temperature conditions.

The term "unit volume" as used herein refers to the maximum volume (v) of composition for an individual injection when treating BPH. In most cases there is a plurality of unit volumes of a composition per patient. For example, there can be n=2, 3, 4, 5, 6, or more, depending on the size of the prostate, which can be determined from ultrasound imaging prior to treatment. Herein, n is the number of unit volumes. The larger the size of the prostate, generally speaking, the higher the number of unit volumes dispensed from a needle at different locations of the prostate. It was found in pre-clinical studies that a prostate treatment using a unit volume of 0.05 ml to 0.1 ml of composition can result in significant reduction in prostate size over a 90 day period. Moreover, it is believed that a unit volume of 0.05 ml to 0.5 ml, 0.05 ml to 0.1 ml, 0.1 to 0.2, or 0.05 to 0.2 ml will also produce positive clinical outcomes with no adverse indications.

From a pre-clinical study in canines with prostate volumes ranging from 19.5 to 44.1 cc's (average 30 cc's), discussed in greater detail, infra., a unit volume of from 0.050 to 0.100 mL and total injected amount for a prostate for 2 unit volume injections of 0.100 mL and 0.200 mL, respectively, produced the desired result (human prostate volumes are typically between 20 to 80 cubic centimeters) or grams (prostate mass density can be approximated as 1 g/cc). In this study local retention of the drug and drug effect was observed and there was no damage to surrounding organs, and there was reduction in prostate volume at 30 and 90 days post SRF treatment.

Normal adult human prostates weigh approximately 20-25 g. A majority of BPH prostate sizes are 30 g or larger with most ranging between 30-80 g. To achieve approximately a >25% reduction in size, the number (n) of unit volumes (v) injected per prostate may be selected based on prostate size. Therefore, in order to reduce a larger size prostate by the same amount, an increased number of unit volumes may be utilized. For example, the number (n) of unit volumes injected to achieve greater than 15%, or greater than 25% reduction in prostate size may be determined from TABLE 1.

TABLE 1

| Prostate Size (g or cc) | # Unit Volumes Injected Total (in both lobes) |
| --- | --- |
| 20-40 | 2-4 |
| 40-60 | 2-6 |
| 60-80 | 4-8 |
| >80 | 6-10 |

The term "total volume" of composition (i.e., the sum of n unit volumes of composition injected into the prostate during a single treatment session, defined as within a 1-2 hours of, or within 24 hours of each other) is the total volume of composition administered to the patient and expected to produce a programmed, sustained release and efficacious outcome when treating BPH. This programmed, sustained release and efficacious outcome may be measured using the International Prostate Symptom Score (IPSS), or more generally relieving Lower urinary tract symptoms (LUTS) include voiding or obstructive symptoms such as hesitancy, poor and/or intermittent stream, straining, feeling of incomplete bladder emptying, and storage or irritative symptoms such as frequency, urgency, urge incontinence, and nocturia. A total volume is expected to produce more than a 15% reduction in prostate volume, or more than a 25% reduction in prostate volume. According to the pre-clinical study using canine models, prostate volumes were reduced by up to 30% over a 30 to 90 day period (canine prostate sizes ranged from 19.5 to 44.1 cc, with average being 30 cc at treatment, and averages being 10 cc at 30 and 90 days after treatment). In some embodiments, the number, n, of a unit volume, v, needed to attain a total volume of composition for prostate treatment is related to the prostate volume, PV as n=PV/(200*v) (rounded to nearest integer). For example, a prostate volume of 30 cc, and unit volume of 0.07 ml gives 2.14, which then gives n=2.

The term "sustained release formulation (SRF)" as used herein refers to a substance for treating BPH, the substance including a drug (or drugs), solvent for the drug and carrier for the drug(s) or drug carrier comprising a polymer composition administered to the target tissue in liquid, gel or solid form using a delivery vehicle, such as a needle syringe, whereupon local delivery of the composition (comprising the SRF) to the target tissue the SRF is effective in producing a sustained release of the drug(s) to the targeted tissue of the prostate, thereby producing an efficacious result over a period of time, e.g., from 14 days, 30 days, 1 to 3 months, up to 6 months, up to 12 months, or up to 2 years following treatment and with minimal uncontrolled drug diffusion. Other substances may also be present in the composition (e.g., an ultrasound/echoing enhancing medium or other imaging enhancing depending on the imaging modality used). A programmed, sustained release of, e.g., from 14 days or 1 to 12 months for substantially all of the drug to dissipate from the carrier is achieved by selection of drug carrier (polymer composition) and/or modifying the morphology and mechanical properties, the polymer/drug ratio, and controlling the physical shape/dimensions (volume) of the SRF and/or composition that is delivered to the target tissue. Other factors influencing a release rate are described in greater detail, below.

The term "target tissue" as used herein is defined as prostate tissue to include the transition zone, peripheral zone and central zone of the prostate, and the prostate.

The most common types of prostate treatment are treatments for cancerous or pre-cancerous conditions (i.e., non-malignant tumors) and enlarged prostate, more commonly known as benign prostatic hyperplasia/hypertrophy (BPH). The tissue types are very different between treatments for cancer or pre-cancerous tumors vs. BPH, which calls for different formulations of a similar drug that may be effective in treating either condition. Most notably, the volume of drug (on a per-volume of prostate basis) is very different when treating a tumor or cancer than when treating BPH. Finally, when treating for cancer or tumor one wants to have the full drug release from a carrier quickly, i.e., within the first 24 hours of injecting the composition into the patient. A slow release, in contrast, is intended to mean a full drug release at a minimum of 1-3 months' time from when the composition was injected into the patient.

In some embodiments a patient to be treated has cancer in another part of the body (other than the prostate) but is being treated for BPH according to the disclosure. In some embodiments the patient does not have cancer in another part of the body and is being treated for BPH.

Procedures for treating BPH have demonstrated varying levels of efficacy and are often accompanied by undesirable or adverse effects. For example, TURP produces improved efficacy and improvement in urinary flow rate and symptom score (IPSS) but is invasive with significant side effects including incontinence, urgency, dysuria, acute retention, stricture, ejaculation dysfunction and sexual dysfunction. Water vapor therapy and PUL have demonstrated less sexual dysfunction side effects but are limited to use in smaller BPH prostates less than 80 ml and have shown less efficacy with non-responders and higher retreatment rates compared to TURP. Furthermore, these procedures are invasive and require transurethral access and catheter placement.

Less invasive targeted drug delivery approaches to the prostate zone have been attempted by the transrectal or transperineal routes such as pore forming proteins and peptides in saline formulations with single dosages but demonstrated limited efficacy versus saline placebo in randomized clinical trials. See Indian J Urol. 2008 July-September; 24(3): 329-335. doi: 10.4103/0970-1591.42613, PMCID: PMC2684358, PMID: 19468462; *Injection therapy for prostatic disease: A renaissance concept.* Arash M. Saemi, Jeffrey B. Folsom, and Mark K. Plante. Additionally, alcohol or medications injected into the prostate have been ineffective. Alcohol single injection is very caustic and poorly controls the area of delivery. Medication injection into the prostate has also been ineffective as it is given in a single dose with poor effect. Other attempts to treat prostate using similar drugs and/or peptide drugs have been used. If injected, the injectate did not include a sustained release formulation of the drug and thus a long acting, efficacious response in the target tissue injected would not be exhibited.

While the foregoing methods may show efficacy in reducing BPH, they either require a more invasive procedure (vs. localized treatment using the delivery device as disclosed herein), more frequent treatment due to diffusion or more generalized treatment of BPH raising the possibility of adverse effects because a comparatively high dosage of the drug is needed to treat the area while accounting for leakage or diffusion of the drug to other areas (i.e., at least 2 to 3 times higher dose of the drug compared to the drug dosage in a unit volume of an SRF). Adverse effects may include diminished urinary or sexual function. It is desired to have an effective treatment targeting only the target tissue and nowhere else (e.g., avoiding the bladder, urethra and nerves surrounding the prostate) and to perform the procedure in a less invasive manner for patient acceptance.

With these objectives in mind, the inventors sought to develop a formulation that could be delivered by way of local prostate needle injection and that could overcome the foregoing drawbacks with existing procedures for treating BPH. The formulation developed is the SRF, which is described in greater detail below, followed by several embodiments of the SRF. Embodiments of a device and method for delivering the SRF using the device, which involves use of a needle syringe, is also described.

A SRF for treating BPH, according to the disclosure, is preferably delivered transrectally or transperineally to the target tissue using a needle syringe having a relatively long and narrow needle (for example, a 15 and 20 cm in length needle, and 0.02 cm to 0.12 cm needle lumen, alternatively a needle having a slenderness ratio, defined as needle length divided by lumen diameter, of between 200 and 400 or, more preferably, 250 and 340). The fluid properties and injectate volume requirements of the composition using this type of needle were initially examined to determine whether there were any limitations, special considerations or modifications needed to the SRF (and/or delivery device) for delivery of this injectate to a prostate.

The question asked was whether the SRF could be delivered to the prostate on a consistent, repeatable basis to ensure a total volume by prostate size is substantially met, but not exceeded, by an administering health professional, to achieve the desired outcome (reduction in prostate volume, over a period of time by a programmed, sustained release of a drug) and without adverse indications (e.g., infection, post-treatment pain or discomfort, drug diffusion into nearby areas such as the urethra or bladder). The inventors found, after extensive bench testing and evaluation of several trials of both delivery device and candidate SRF formulations, a needle syringe suited to deliver the SRF in the manner sought by the inventors.

Figure 3C:
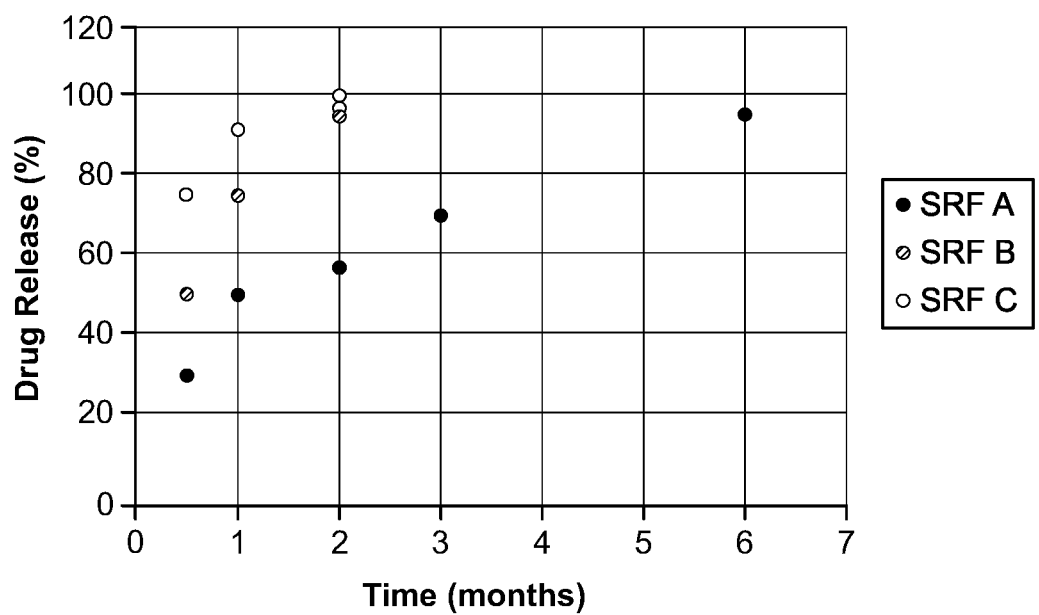
FIG. 3C shows Drug Release Curves for SRFs A, B and C.
Figure 4:
FIG. 4 shows a histopathology H&E staining microscope image of a sectioned canine prostate lobe 30 days after SRF1 treatment in BPH animal #21C0042. Outline shows necrotic core and extent of drug effect around the 100 uL volume of SRF injectate (arrow). Scale bar equals 1 mm.
Figure 5:
FIG. 5 shows histopathology H&E staining microscope image of a sectioned canine prostate lobe 90 days after SRF1 treatment in BPH animal #21C0046. Outline shows necrotic core and extent of drug effect around the 50 uL volume of SRF injectate (arrow). Scale bar equals 1 mm.
Figure 6:
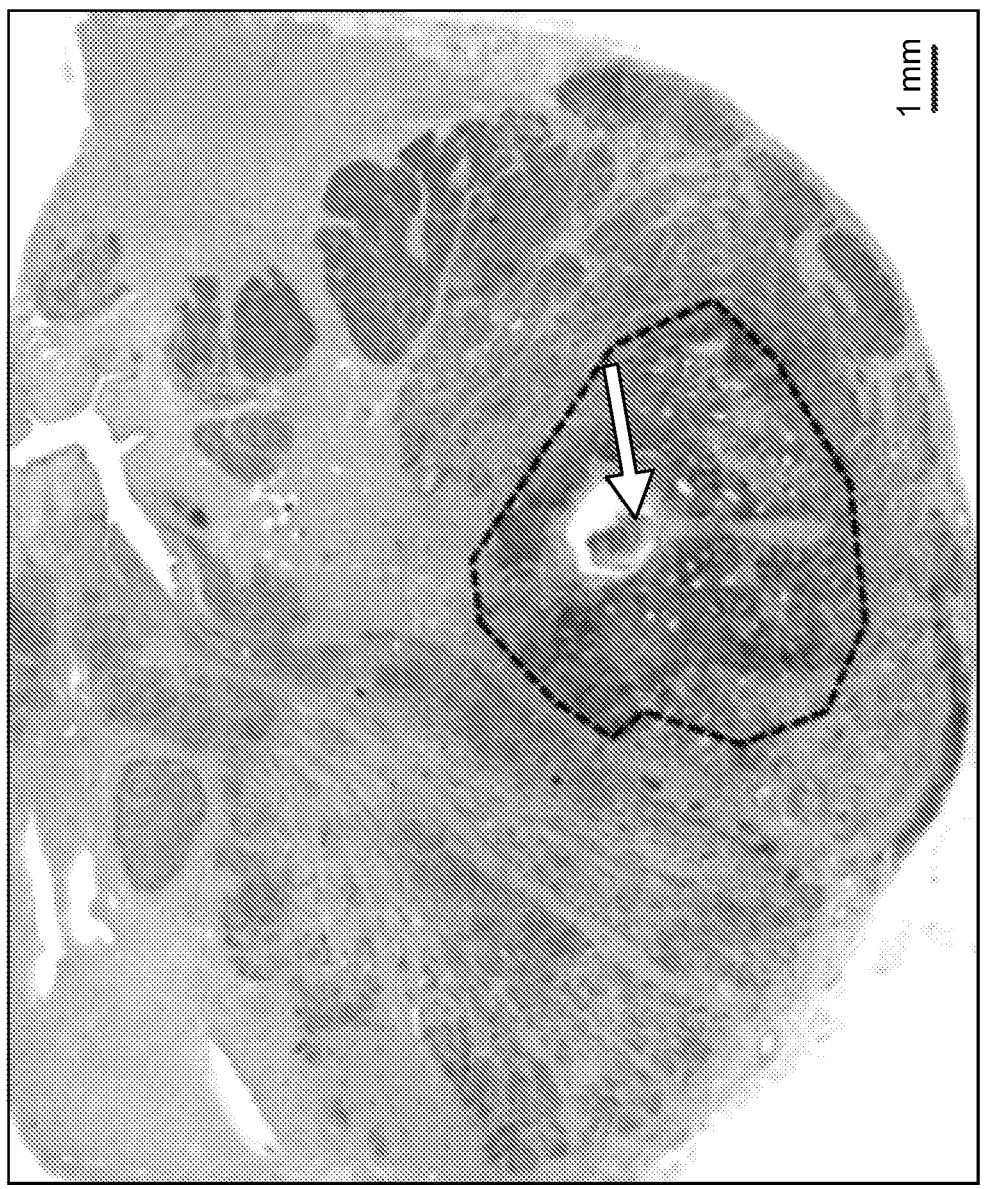
FIG. 6 shows histopathology H&E staining microscope image of a sectioned canine prostate lobe 90 days after SRF1 treatment in BPH animal #21C0050. Outline shows necrotic core and extent of drug effect around the 50 uL of volume of SRF injectate (arrow). Scale bar equals 1 mm.

A prostate treatment according to the disclosure may be described as a prostate treatment having three characteristics:

1. MINIMAL UNCONTROLLED DRUG DIFFUSION: Obtaining sufficient solidification or gelation of the SRF in a relatively short period of time upon contact with the prostate, so that the SRF remains at the target tissue when the needle is removed and, hence, little or no drug diffusion takes place possibly affecting unintended, adjacent tissue such as the urethra or bladder (e.g., as demonstrated by the little or no drug diffusion outside of the prostate for the canine models studied, see TABLE 8).
2. SUSTAINED RELEASE & EFFICACY: Enabling a programmed release of a drug over time from the SRF (see e.g., FIG. 3C, TABLES 4A and 4B). The SRF is delivered in a sufficient total volume to enable a sustained release of a drug for prolonged treatment of the target tissue to achieve the efficacious result of reduced prostate size.
3. LOW UNIT VOLUME: Delivery of the composition total volume to the prostate as one or more low unit volumes (i.e., "unit volume" as defined herein) using a needle syringe. This manner of delivery avoids causing additional acute pressure on the urethra, which may cause additional discomfort for the patients immediately after or shortly after the procedure, or to avoid excessive swell due to uptake of fluids from the surrounding tissue. Additionally, a low unit volume of the composition avoids pressure at the injection site, which can mitigate against composition flow to surrounding tissues and organs and/or backflow of the composition through the delivery device or through the needle track once the needle is removed, and/or inhibiting the composition from being expelled from the target tissue due to pressure buildup. It can also be desirable to have a low unit volume injected at several discrete, nearby locations to achieve the targeted clinical outcome, as this can optimize diffusion of a hydrophobic drug relative to diffusion from a large volume injected in one location.

The factors influencing, and manner of arriving at the SRF formulation and composition enabling a prostate treatment with these characteristics will now be discussed. More specific examples of embodiments of an SRF are provided later.

Drug to Polymer Ratio. The drug to polymer ratio for the SRF formulation was investigated, as well as the drug to solvent ratio. Too low of a drug to polymer ratio is not attractive. If the drug dosage is too low, then it results in the local drug concentrations being too low. Too high of a drug to polymer ratio results in the drug releasing from the SRF too fast which limits the longer term local drug release and also leads to surrounding tissue and/or systemic drug exposure.

Polymer to Solvent Ratio and Polymer Molecular Weight. The polymer to solvent ratio and polymer molecular weight associated with the SRF formulation were investigated. Too low of a polymer to solvent ratio is not attractive. If the polymer concentration and or molecular weight are too low, then it results in slow gelation and the drug releasing from the SRF too fast which limits the longer-term local drug release and also leads to surrounding tissue and/or systemic drug exposure. As discussed in greater detail below, the desire to achieve a high gelation rate was balanced against the need for deliverability using a needle characterized by a high slenderness ratio. Too high of a polymer to solvent ratio and molecular weight results in a composition having a high viscosity, which may be delivered safely when using needles characterized by low slenderness ratios and in relatively large volumes. But the same polymer to solvent ratio and molecular weight can pose a significant challenge to deliver in unit volume amounts using needles characterized by a high slenderness ratio, in addition to the challenge of determining whether that selected polymer to solvent ratio and molecular weight produces the desired gelation rate without also producing too-slow of a drug release. It was these types of trade-offs or balances that led the inventors to identify an optimal combination of needle and composition, which is represented by the KIR.

It should be noted that the above-mentioned ratios and polymer molecular weights (examples provided below) are easily determined for the clinical use intended here; rather, it required lengthy investigation and discovery in order to arrive at the desired localized efficacy and effectiveness specifically tailored to satisfy all three characteristics of prostate treatment.

It is desired to have a programmed, sustained release of, e.g., 14 days or 1 to 12 months for substantially all of the drug to dissipate from the carrier. This requires the selection of the drug carrier (polymer composition) and/or modifying the morphology and mechanical properties, the polymer/drug ratio, controlling the physical shape/dimensions (volume) of the SRF and/or composition delivered to the target tissue. Other factors affecting the release rate include:

ability of polymer to swell (controlled by polymer structure e.g., monomers selection, monomer ratios, molecular weight, end groups, and porosity/morphology).

porosity/morphology (controlled by e.g., polymer structure and concentration, polymer/solvent ratio and miscibility, and polymer/drug ratio-less drug than polymer than drug is trapped).

how fast the materials gel and whether above or below wet glass transition temperature—transition from liquid to solid using water soluble or insoluble solvents (fast gelation leads to faster initial release/burst) (controlled by e.g., polymer structure and concentration, polymer/solvent ratio and miscibility).

polymer degradation (controlled by polymer structure e.g., monomers selection, monomer ratios, molecular weight, end groups, and porosity/morphology).

drug/polymer miscibility and polarity of solvent, and molecular weight and lipophilicity of drug.

TABLE 2 examples of compositions
Examples of constituents by % vol in a composition comprising SRF

| Example | Drug | Polymer | SRF (drug & polymer %) | SRF (solvent %) |
|---|---|---|---|---|
| 1 | Paclitaxel (4.3%) | PLGA 50/50 (47.8%) | 52.1% (polymer + drug) | NMP 47.8% |
| 2 | Sirolimus (4.3%) | PLGA 85/15 (47.8%) | 52.1% (polymer + drug) | NMP 47.8% |
| 3 | Paclitaxel (3.6%) | PLGA 50/50 (48.2%) | 51.8% (polymer + drug) | NMP 48.2% |
| 4 | Sirolimus (3.4%) | PLGA 85/15 (48.3%) | 51.8% (polymer + drug) | NMP 48.3% |
| 5 | Paclitaxel (5.0%) | PLGA 50/50 (47.5%) | 52.5% (polymer + drug) | NMP 47.5% |
| 6 | Sirolimus (5.0%) | PLGA 85/15 (47.5%) | 52.5% (polymer + drug) | NMP 47.5% |
| 7 | Sirolimus (7.0%) | PLGA 50/50 (46.5%) | 53.5% (polymer + drug) | NMP 46.5% |
| 8 | Sirolimus (7.0%) | PLGA 85/15 (46.5%) | 53.5% (polymer + drug) | NMP 46.5% |
| 9 | Paclitaxel (7.0%) | PLGA 50/50 (46.5%) | 53.5% (polymer + drug) | NMP 46.5% |
| 10 | Paclitaxel (7.0%) | PLGA 85/15 (46.5%) | 53.5% (polymer + drug) | NMP 46.5% |
| 11 | Sirolimus (8.0%) | PLGA 50/50 (37.5%) | 45.5% (polymer + drug) | NMP 54.5% |
| 12 | Sirolimus (8.0%) | PLGA 85/15 (37.5%) | 45.5% (polymer + drug) | NMP 54.5% |
| 13 | Paclitaxel (8.0%) | PLGA 50/50 (37.5%) | 45.5% (polymer + drug) | NMP 54.5% |
| 14 | Paclitaxel (8.0%) | PLGA 85/15 (37.5%) | 45.5% (polymer + drug) | NMP 54.5% |
| 15 | Sirolimus (9.0%) | PLGA 50/50 (40.0%) | 49.0% (polymer + drug) | NMP 51.0% |
| 16 | Sirolimus (9.0%) | PLGA 85/15 (40.0%) | 49.0% (polymer + drug) | NMP 51.0% |
| 17 | Paclitaxel (9.0.%) | PLGA 50/50 (40.0%) | 49.0% (polymer + drug) | NMP 51.0% |
| 18 | Paclitaxel (9.0%) | PLGA 85/15 (40.0%) | 49.0% (polymer + drug) | NMP 51.0% |
| 19 | Sirolimus (10.0%) | PLGA 50/50 (40.0%) | 50.0% (polymer + drug) | NMP 50.0% |
| 20 | Sirolimus (10.0%) | PLGA 85/15 (40.0%) | 50.0% (polymer + drug) | NMP 50.0% |
| 21 | Paclitaxel (10.0%) | PLGA 50/50 (40.0%) | 50.0% (polymer + drug) | NMP 50.0% |
| 22 | Paclitaxel (10.0%) | PLGA 85/15 (40.0%) | 50.0% (polymer + drug) | NMP 50.0% |

TABLE 2-continued examples of compositions
Examples of constituents by % vol in a composition comprising SRF

| Example | Drug | Polymer | SRF (drug & polymer %) | SRF (solvent %) |
|---|---|---|---|---|
| 23 | Sirolimus (12.0%) | PLGA 50/50 (35.0%) | 47.0% (polymer + drug) | NMP 53.0% |
| 24 | Sirolimus (12.0%) | PLGA 85/15 (35.0%) | 47.0% (polymer + drug) | NMP 53.0% |
| 25 | Paclitaxel (12.0%) | PLGA 50/50 (35.0%) | 47.0% (polymer + drug) | NMP 53.0% |
| 26 | Paclitaxel (12.0%) | PLGA 85/15 (35.0%) | 47.0% (polymer + drug) | NMP 53.0% |

The composition may include a bioabsorbable polymer at a concentration of 20-80%, 25-75%, 40-60% by wt. of the bioabsorbable polymer composition, 80-20%, 75-25%, 60-40%, by wt. of the solvent and 0.5%-30% by wt. drug; 1%-20% by wt. of drug, or 1%-5% by wt. of drug.

Number of injections/injection total volume. In a first pre-clinical canine study composition was delivered to the prostate by needle injection as a single, relatively large volume with some observed backflow through the needle. This approach resulted in injectate being diffused away from the target tissue, which is undesirable for reasons previously stated. In response, in the second pre-clinical canine study (below) the inventors instead tried a low injection volume of composition, minimized between 10-200 microliter per injection over 1-10 injections across each side of the prostate to reduce prostatic tissue pressure on the urethra to mitigate any potential backflow through the delivery device and/or loss of therapeutic injectate from the target tissue. A further injection volume range 50-100 microliter per injection over 1-5 injections across each side of the prostate was studied. The low unit volume injections are designed to minimize swelling and bulking of the prostate.

The low and distributed unit volume approach adopted (third characteristic) also produced an unexpected efficacious benefit. The second pre-clinical study, discussed infra., achieved a greater than 30% reduction in prostate size in the canine models. Notably, in the first study a higher volume of drug (by prostate weight) was used, compared to the total volume of drug in the second study. The SRF also was distributed throughout the prostate in unit volumes in the second study, but the total volume of drug (by prostate weight) in the second study was less than that used in the first study. This indicates that using smaller unit volumes distributed throughout reduces prostate size more effectively than injecting a relatively higher unit volume at one location, which is a typical approach taken by others treating BPH. The distributed low unit volume composition approach also showed controlled drug diffusion away (i.e., minimal drug lost to surrounding tissues and circulation) from the treatment area (see FIGS. 7 and 8 and accompanying text summarizing results).

In addition to the search for a composition that could satisfy the first two of the three characteristics sought by the inventors (minimal uncontrolled drug diffusion, sustained release rate and efficacy), there was the concomitant need to determine what kind of needle syringe could deliver the total volume of composition effectively, in a repeatable manner as one or more low unit volumes without the need for compromising the effectiveness of the SRF once injected. Thus, investigation into the deliverability of the composition to a patient was also needed.

A long, narrow needle (e.g., 20 cm with 0.06 cm lumen size) is desired as the manner for delivering the composition to the target tissue. Because it is a less invasive approach to accessing the target tissue than other methods for treating BPH and is more likely to be acceptable by patients in general. But use of this type of delivery device presented special challenges that needed to be overcome before the three characteristics of prostate treatment could be satisfied when using this delivery device.

Delivery of a SRF, a composition characterized by a relatively high viscosity for dispensing from a needle, is challenging when using a long, narrow needle of high slenderness and when dispensed in small volumes, due to the liquid shear stresses influenced by the needle inner surface area. The resistance to flow by a composition pushed through a long and narrow needle becomes more acute and deserving of attention the more viscous the liquid. Accordingly, for a relatively high viscosity fluid, which is more influenced by wall-fluid shearing stresses than a less viscous fluid, the inaccuracy in volume dispensed from a needle is more pronounced and varies proportionately with needle slenderness (defined as needle length, L, divided by lumen diameter, D). Accordingly, since the inaccuracy of volume delivered varies proportionately with L/D and directly with the composition's viscosity, the smaller the dispensed volume desired and more viscous the composition, the more the inaccuracies are expected. The inventors, realizing this challenge to overcome with accurately dispensing the viscous composition for prostate treatment, had to identify both the embodiments of composition satisfying the first two characteristics (minimal uncontrolled drug diffusion, sustained release rate and efficacy requirements) and the needle syringe(s) that when used by a health professional enabled him/her to satisfy the third characteristic (low unit volumes distributed over the prostate to attain the total volume of composition), without unduly compromising SRF effectiveness when introduced into the prostate.

On the one hand, bench tests indicated promising SRF formulations, but the corresponding compositions could not be reliably delivered using a long narrow needle. On the other hand, when the viscosity of the composition was reduced to make it easier to dispense the composition at the desired unit volume, either the desired drug release profile and/or gelation rate would not be achieved, or there would be an unacceptable level of drug diffusion into adjacent tissue or organs. Either the drug eluted too quickly from the SRF, the polymer gel was not dense or entangled enough, or the gelation rate was not high enough to avoid injectate flowing back to the needle and being drawn back along with the needle, away from the target tissue, after completion of the injection.

Thus, a careful balancing of constituents in the formulation—a polymer structure and molecular weight and concentration with a drug ratio and dose and solvent ratio to produce a desirable SRF with controlled release (e.g., as shown in FIG. 1, Table 1)—was eventually accomplished. But then it was found that the desired composition could not be delivered reliably as several low unit volumes using a long needle as required to treat the prostate. Not infrequently, a more preferred, viscous formulation would need to be abandoned for a less viscous formulation to ensure that the right unit volume of composition with desired drug release could be repeatedly delivered using a long and narrow needle.

SRF1, which was used in the second pre-clinical study, discussed below, is an example of a SRF that satisfied the first two characteristics (minimal uncontrolled drug diffusion, sustained release rate and efficacy) and was capable of being accurately and repeatedly delivered in low unit volumes, thereby also satisfying the third characteristic of prostate treatment.

Figure 7:
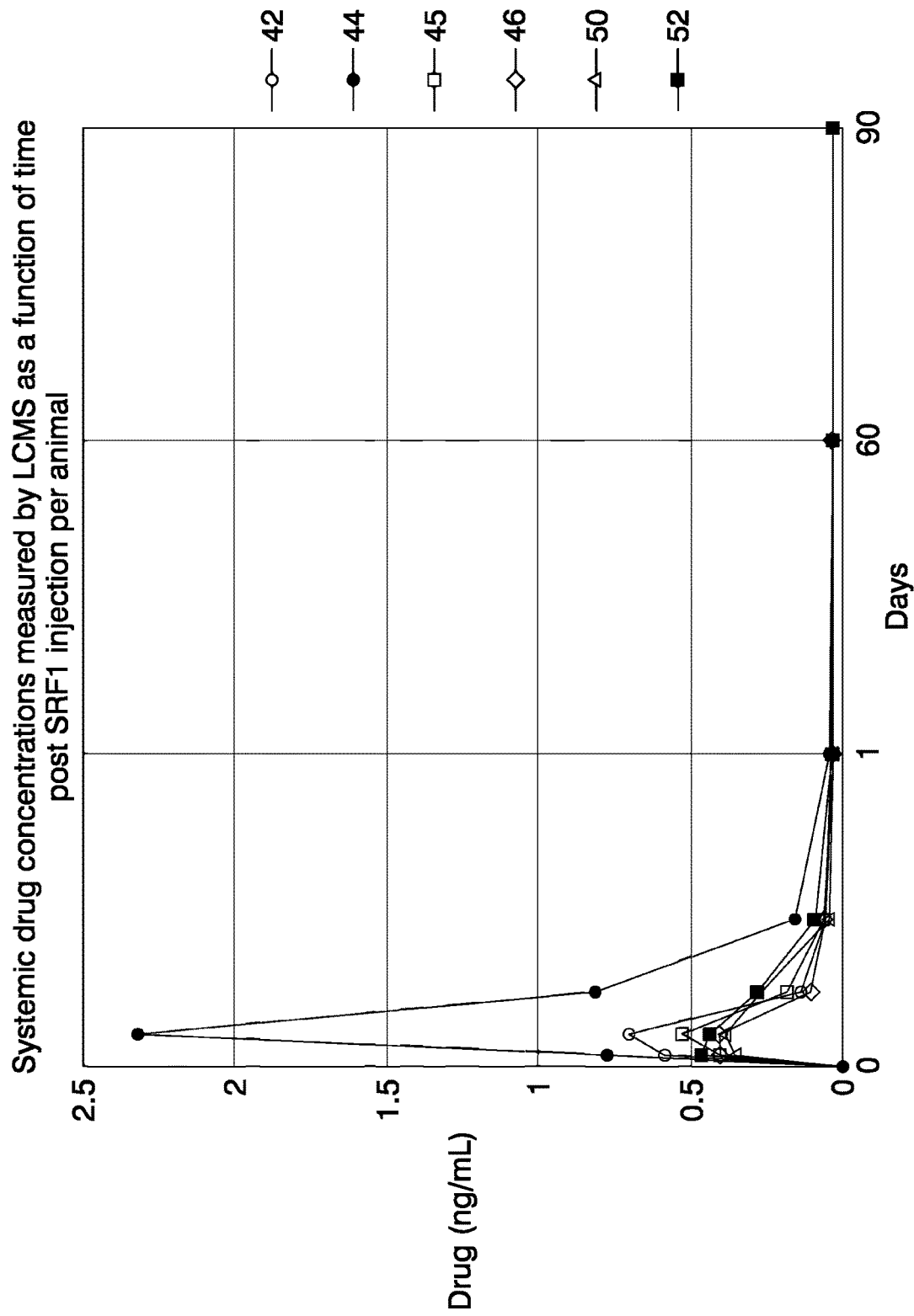
FIG. 7 shows systemic drug concentrations measured by LCMS as a function of time post of a SRF1 injection per animal.
Figure 8:
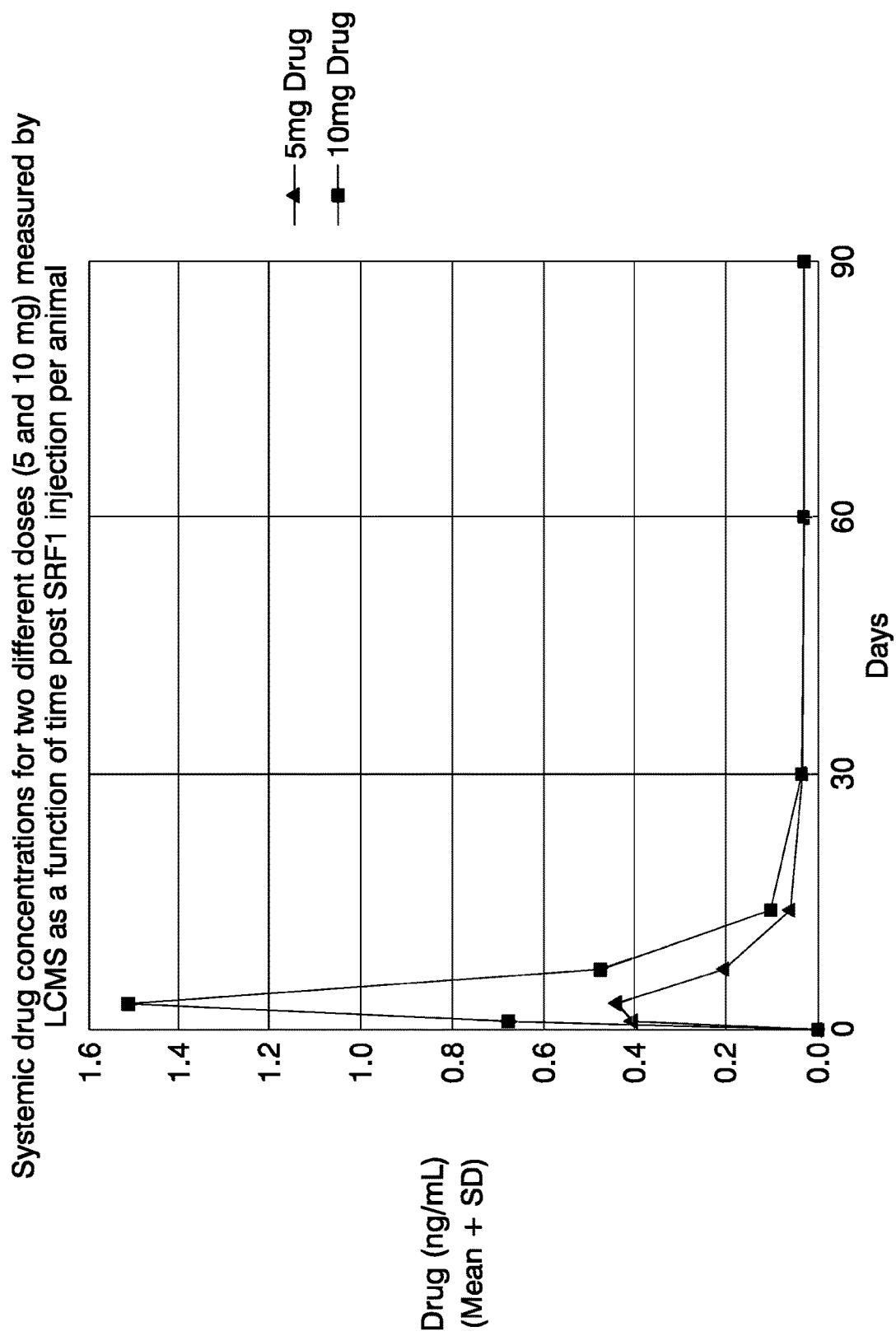
FIG. 8 shows systemic drug mean concentrations measured by LCMS (liquid chromatography/mass spectrometry) as a function of time post SRF1 injection per animal as a function of drug dosage. N=6 for 0 to 30 days and N=3 60 days and 90 days, 4 animals with 5 mg and 2 animals with the 10 mg initiation.
Figure 9:
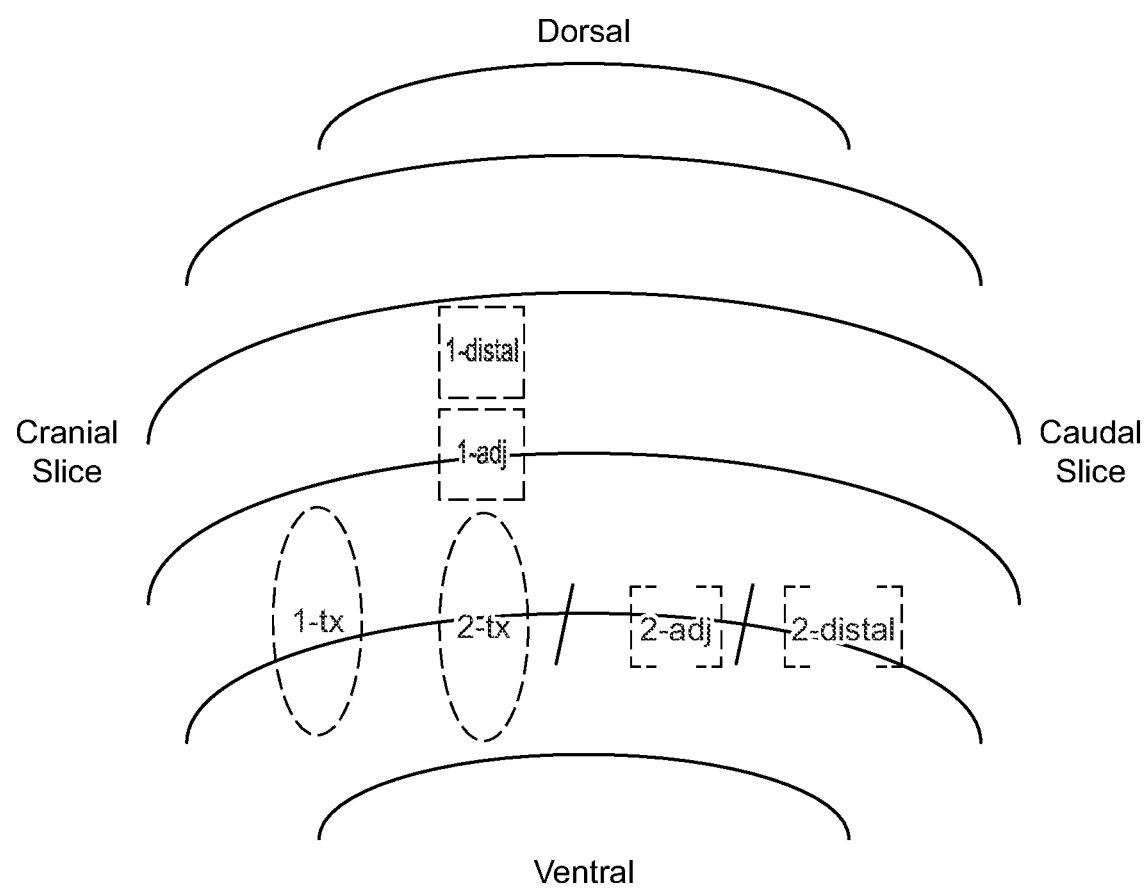
FIG. 9 shows locations for injection of SRF1 in a prostate. It shows the locations in TABLE 7 for collecting prostate samples for pharmacokinetic ("pk") tissue analysis. Circles indicate treatment samples ("tx"), rectangles indicate either adjacent reference samples ("adj") or distal reference samples ("distal"). Numbers in diagram are the locations corresponding to TABLE 7.

Two unit volumes (0.05 ml and 0.10 ml) were considered in the pre-clinical study. Both injection volumes showed significant reduction in prostate size, as reported in TABLES 5 and 6. Additionally, as shown in FIGS. 7 and 8, there was very low systemic drug concentrations present in the blood, indicating that the agent was contained at the target tissue. The pre-clinical study therefore indicates that an SRF injectate according to the disclosure can (1) reduce prostate volume over a 30 and 90 day period, and (2) limits substantially all of the active agent to only the target tissue. Moreover, the study indicated unexpectedly a significant ratio of prostate 30-day and 90-day drug concentration to maximum plasma drug concentration of at least 10,000. A comparatively small volume of SRF injectate needed for efficacy was also demonstrated. SRF (SRF1) injectate was minimized to between 10-200 microliter per injection over 1-10 injections across each side of the prostate, or 50-100 microliter per injection over 1-5 injections across each side of the prostate.

As for compositions comprising the SRF, drug and polymer concentrations in the composition may range from 0.1 wt % up to 60 wt %. Injection volumes of the SRF may range from 25 microliters up to 5 mL per injection. Overall dosage of drug provided in the SRF can range from 50 ug up to 200 mg. For example, a composition comprises 300 ug of sirolimus dissolved with 3,000 ug ("ug"-micrograms) poly (D, L-lactide-co-glycolide) (85:15) in NMP at an about 50 solid wt. % concentration, a composition, a composition comprises 300 ug of paclitaxel dissolved with 3,000 ug ("ug"-micrograms) poly (D, L-lactide-co-glycolide) (85:15) in NMP at an about 50 solid wt. % concentration, a composition comprises 500 ug of sirolimus dissolved with 2,900 ug ("ug"-micrograms) poly (D, L-lactide-co-glycolide) (85:15) in NMP at an about 50 solid wt. % concentration, a composition comprises 500 ug of paclitaxel dissolved with 2,900 ug ("ug"-micrograms) poly (D, L-lactide-co-glycolide) (85:15) in NMP at an about 50 solid wt. % concentration, a composition comprises 300 ug of sirolimus dissolved with 3,000 ug ("ug"-micrograms) poly (D, L-lactide-co-glycolide) (50:50) in NMP at an about 50 solid wt. % concentration, a composition, a composition comprises 300 ug of paclitaxel dissolved with 3,000 ug ("ug"-micrograms) poly (D, L-lactide-co-glycolide) (50:50) in NMP at an about 50 solid wt. % concentration, a composition comprises 500 ug of sirolimus dissolved with 2,900 ug ("ug"-micrograms) poly (D, L-lactide-co-glycolide) (50:50) in NMP at an about 50 solid wt. % concentration, and a composition comprises 500 ug of paclitaxel dissolved with 2,900 ug ("ug"-micrograms) poly (D, L-lactide-co-glycolide) (50:50) in NMP at an about 50 solid wt. % concentration. As used herein, the term solvent refers to a solvent capable of fully or homogenously dissolving substances added to the solvent.

Further examples of compositions that satisfy the first two characteristics (efficacy and sustained release, and low diffusion) are provided in the examples, below.

Precise delivery of low volumes of a SRF for therapeutic retention with a precise drug dosage may be accomplished using a 250-500, or 250-2500 microliter or smaller needle syringe. This delivery device may have a gastight, glass or polypropylene syringe body with Teflon or polypropylene plunger connected with a 20 cm long 22 g needle, which has a 0.06 cm lumen diameter. The volume of the delivery syringe must be large enough to accommodate the dead volume within the needle of approximately 150 microliter. Therefore, a 250 microliter gastight syringe can be utilized to deliver one to two 50 microliter unit volumes of a composition. For multiple injections from the same delivery device a 250-1,000 microliter gastight syringe volume may be used, which allows sufficient volume to overcome needle dead volume and can deliver at least eight 100 microliter unit volume injections to each lobe of a prostate.

Referring to FIG. 1, a typical needle syringe includes an applicator portion (plunger, barrel), and hub portion that connects the needle with the interior chamber of the barrel and forms a fluid-tight connection for passage of a fluid contained within the barrel through the needle lumen.

Figure 2A:
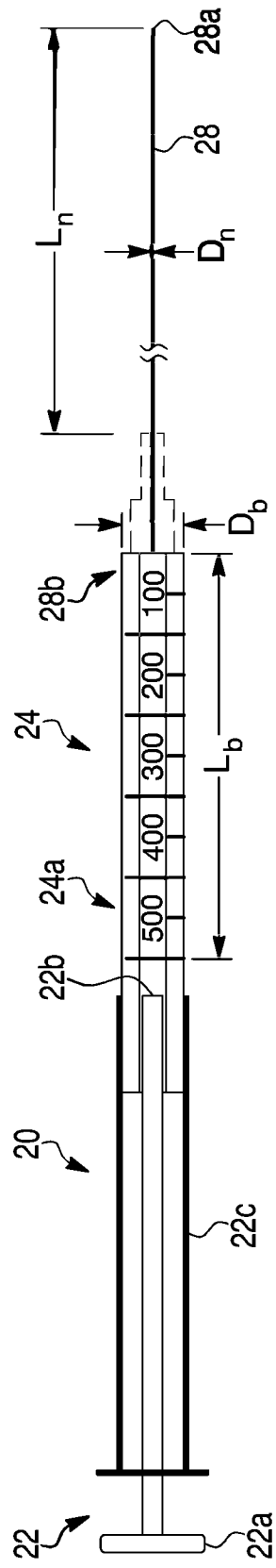
FIGS. 2A, 2B are schematic side-view illustrations of needle syringes for delivering a composition comprising a sustained release formulation (SRF).
Figure 2B:
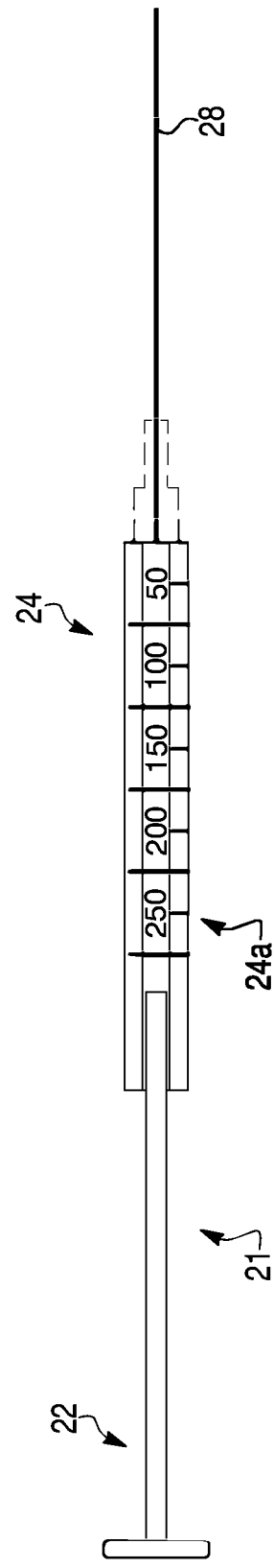

Referring to FIGS. 2A and 2B, there is shown side view schematics of needle syringes 20, 21 according to the disclosure. More specifically, the needle syringes depicted have sizes for holding and dispensing a unit volume through a long, narrow needle tip 28a. The needle 28 is characterized by a length $L_n$ and lumen diameter $D_n$ (a needle hub is shown in phantom for the sake of illustrating the measured length $L_n$, which is taken from the upstream opening 28b forming the fluid-tight connection between the barrel and needle 28 body and the terminal, or downstream-most tip that first punctures the skin). The needle may be made from stainless steel.

The needle syringe in FIG. 2A shows by example gradations of 500/400/300/200/100 micro-liters for dispensing unit volumes of e.g., 0.05 ml (50 micro-liters). The barrel capacity is 500 micro-liters. The barrel 24 has a length $L_b$ and barrel inner or lumen diameter $D_b$. The prefilled syringe barrel (500 micro-liter) may have attached to it a needle length $L_n$ of 20 cm and the barrel may have a 150-200 micro-liter dead volume. The syringe, which may need to be prefilled, may also incorporate a stabilizer 22c for guiding the plunger head 22b towards the needle opening 28b. The composition comprising the SRF (contained in the syringe barrel 24 and in amounts up to about 500 micro-liters) is ejected through the needle tip 28a by finger pressure applied to the plunger head 22a. In this example, the barrel, when holding 500 micro-liters of composition can hold, for example, up to 7, 50 micro-liter unit volumes accounting for the 150 micro-liter dead volume. The needle syringe in FIG. 2B is the same in several respects as the syringe in FIG. 2A, except that it has instead a 250 micro-liter barrel capacity. It may also incorporate a stabilizer 22c. In another example a 250 micro-liter capacity syringe has graduations of 50 uL, 25 uL, 5 uL and 2.5 uL to help with more accurately dispensing low unit volumes of the composition.

The syringes in FIGS. 2A and 2B are sized to enable a medical professional to accurately dispense unit volume amounts (e.g., 0.05 ml or 0.1 ml) at discrete/separate locations within a target tissue. The syringe may be pre-filled to hold a sufficient total volume for fully treating a patient (e.g., 4 unit volumes injectate at different locations in the prostate tissue). In some embodiments, an applicator portion may include syringe chambers for holding the SRF drug and drug carrier separate from each other, a mixing element for combining the drug and drug carrier such as a static mixing Y-adapter that feeds into a narrow and long, or high slenderness (L/D) ratio needle 28. Alternatively, the drug, drug carrier, and solvent may be mixed using two syringes connected with an adapter, with back and forth plunging to mix the drug, drug carrier, and polymer. The applicator portion may have markings demonstrating measurement of lengths of needle insertion or composition volume.

The syringe control needed for dispensing unit volumes of a composition comprising a SRF from the barrel 22 through the needle tip 28 becomes challenging either when a long narrow needle is used, or individual injections do not exceed a unit volume amount. Both of these things are present according to the disclosure, as explained earlier. It was found that for the ranges of SRF formulations found suitable to achieve the goals of treatment and being deliverable in a composition in unit volume amounts, the following values for $L_b$, $D_b$, $L_n$, and $D_n$ can apply. The needle length $L_n$ may be from 10 to 30 cm, more preferably from 15 to 20 cm. The lumen diameter $D_n$ may be 0.06 cm, or between 0.06 and 0.08 cm, and in some embodiments 0.02 cm up to 0.12 cm. The needle's slenderness ratio ($L_n/D_n$) may be between 200 and 400, or between 250 and 350.

The barrel length $L_b$ may be from 5 to 20 cm, more preferably from 5 to 10 cm. The barrel lumen diameter $D_b$ may be 0.2 to 0.5 cm.

In some embodiments, the syringe barrel's slenderness ratio ($L_b/D_b$ may be 5 and 50, or between 10 and 30) is an important factor to consider. Barrel slenderness ratios in these ranges were found to help with more accurately dispensing low unit volumes of the composition.

A desired injection volume control and precision custom elongated glass body gastight delivery syringe can be utilized that provides increased accuracy of volume graduation markings on the syringe. Instead of volume graduations these delivery device markings can also show directly the needle calibrated dead volume and drug delivery drug dosage in mg for each injection for the user.

The pre-filled syringe preferably contains the composition as a pre-mixed solution for each injection, which results in delivery of a primarily amorphous drug already dissolved in the polymer carrier for faster drug release and enhanced onset of efficacy then later slower sustained release of drug.

In some embodiments, an SRF can be provided with polymer injectate and drug powder in the separate delivery syringes (mentioned above) mixed by the user on or about the time of treatment and placed into the syringe barrel. This would allow for a mostly or partially crystalline drug directly into the injectate to increase drug retention time and exposure time and reduce systemic drug loss given that some drug would remain in a powdered crystalline form after user preparation.

In some embodiments, An SRF generating composition can be mixed with an ultrasound microbubble contrast agent to further enhance visibility of injectate under transrectal ultrasound guidance to enable precise location control of injection within a prostate capsule within each lobe of a prostate to further minimize potential for drug loss to the urethra, surrounding organs and systemic circulation.

During the course of testing different formulations for an efficacious SRF, the inventors had sought to find a parameter or relationship that they could use to discount a formulation as unsuitable because it could not be delivered reliably. This was much needed because the iterative process of conceiving a certain formulation then evaluating whether it, in combination with the delivery vehicle could satisfy all three characteristics of prostate treatment was a long process. To find a formulation that eventually met those requirements, only to find out that it could not be reliably delivered in the small volumes needed using a long narrow needle, made the process much more labor intensive.

Moreover, it should be emphasized that the objective in matching a composition with a needle syringe was to not compromise more than needed, on the effectiveness of the SRF, in order to ensure its deliverability. The inventors sought an advantageous solution, not simply a way to save time or reduce the amount work needed to match an acceptable SRF with a delivery device. Unexpectedly, it was discovered that there is a numerical range to inform whether a unit volume v of a composition comprising an SRF (as represented by its absolute viscosity p) can be accurately and repeatedly delivered using a needle with length L and lumen diameter D.

When adopting this numerical range as a requirement for the syringe needle with composition, in addition to the required three characteristics for prostate treatment, a more effective SRF formulation is found, because the value addresses the deliverability problem and without unnecessarily compromising the SRF effectiveness. The numerical range is computed using the K-Injectate Rating or KIR, defined as follows:

$$KIR = \frac{\mu L^2}{vD}(10^{-6})$$

For a KIR between 40 and 400, with units of centipoise (cP) per unit area, one may conclude that the SRF can be reliably and consistently delivered in unit volume increments using a needle having a length L, lumen diameter D, a composition's absolute viscosity µ and a unit volume v. The KIR is defined for L from 10 to 30 cm, more preferably from 15 to 20 cm, a lumen diameter D of 0.06 cm, or between 0.06 and 0.08 cm, and in some embodiments 0.02 cm up to 0.12 cm. The needle's slenderness ratio (L/D) may be between 200 and 400, or between 250 and 350.

In some embodiments KIR may be between 10 and 1000. The higher ranges may be preferred in situations where a more delayed release rate and/or higher rate of gelation is desired, as well as smaller unit volumes. A higher KIR may also be preferred for a larger prostate where a longer needle is needed to access the prostate transrectally. In some embodiments KIR may be 10 to 300. A smaller KIR may be preferred for a smaller prostate where a shorter needle is needed to access the prostate, transperineally.

TABLE 3 (shown in FIGS. 3A, 3B) discloses embodiments of an apparatus for delivery of a unit volume of a composition comprising an SRF according to the disclosure.

As explained earlier, it is desirable to use a long, slender needle for injecting the relatively high-viscosity composition comprising a SRF that will produce the efficacious result without concomitant, adverse effects on the patient's health due to diffusion, infection, or pain/discomfort during or after the procedure. And it is also important that the medical professional treating the patient has adequate control over the volume of composition injected to enable the dispensing of a unit volume at each injection site, for volume control is necessary to achieve the desired clinical outcome. The ranges in TABLE 3 for KIR are believed effective in identifying the composition satisfying the first two characteristics for prostate treatment according to the disclosure, and the syringe needle satisfying the third characteristic for prostate treatment according to the disclosure.

The lower end of the KIR range in TABLE 3 represents compositions that while relatively easy to dispense in small unit volumes (for a fixed needle length, e.g., 15 cm), have a minimal amount of viscosity representative of an SRF's ability to satisfy two of the characteristics for prostate treatment (efficacy, sustained release, and minimal uncontrolled drug diffusion), shorter needle lengths and higher unit volumes. The upper end of the KIR range in TABLE 3 represent (for a fixed needle length, e.g., 20 cm) compositions having higher viscosity, longer needle lengths and smaller unit volumes. For these compositions, the two characteristics for prostate treatment will be easily satisfied when the formulation is injected, but the viscosity, if any higher, might challenge the health professional's ability to deliver a total volume of composition in unit volume amounts, especially along a longer needle length. As such, the capabilities of the delivery device are limiting for high KIR values.

In addition to KIR, in some embodiments the syringe barrel's slenderness ($L_b D_b$ may be 5 and 50, or between 10 and 30) can be an important factor to consider as well. Barrel slenderness ratios in these ranges were found to help with more accurately dispensing low unit volumes of the composition and may be preferred in order to satisfy the deliverability requirement (third characteristic).

Following description provides additional detailed information on embodiments of an SRF and the various constituents and properties therefore that may be included in a SRF for treating BPH using a needle syringe according to the disclosure.

Drug or drug combinations used in the SRF include a cytostatic drug, cytotoxic drug, and/or other drugs. The other drug(s) may be used by themselves (i.e., the "other drug(s)" are the only active agents in the SRF), or in combination with the cytostatic drug or cytotoxic drug as part of the medical procedure for treatment of BPH. For example, the other drug(s) may be administered before the composition injected into the target tissue using a needle syringe, or the other drug(s) may be included in the composition with the SRF. Or the other drug(s) may be administered after the SRF containing the cytostatic drug or cytotoxic drug is administered to the target tissue.

These other drugs, which may be administered with, or instead of the cytostatic or cytotoxic drug, include alpha blockers or 5-alpha reductase inhibitors. Alpha blockers may include and are not limited to terazosin, doxazosin, tamsulosin, alfuzosin, and silodosin. 5-alpha reductase inhibitors may include and are not limited to finasteride and dutasteride. Anti-inflammatory drugs may include but are not limited to corticosteroids such as dexamethasone, fluticasone propionate, triamcinolone acetonide, mometasone furoate, prednisone, hydrocortisone, estradiol, clobetasol, and budesonide. Non-steroidal drugs may include acetaminophen, ibuprofen, and naproxen. These other drug types may block cytokine activity or inhibit binding of cytokines to inhibit inflammatory signals such as anti-IL1, anti-IL 2, anti-IL3, anti-IL4, anti-IL8, anti-IL15, anti-IL 18, anti-MCP 1, anti-CCR2, anti-GM-CSF, anti-TNF antibodies and others.

Five alpha reductase inhibitors reduce the prostate volume by 50% when given orally. Minimal reduction occurs in less than six months. An up to 50% reduction in prostate volume is expected in 12-24 months or possibly longer with appropriate therapy.

Alpha blockers can also be used to treat symptomatically at the time of procedure by blocking the alpha receptor and relaxing the prostate smooth muscle. Alpha blockers, five alpha reductase inhibitors or both may be co-formulated with cytostatic or cytotoxic drugs in the SRF.

When expressing a % of a substance in the SRF, the % of that substance may be expressed in terms of a percent weight of the drug(s) to the overall weight of the SRF("% X by wgt"), or to the overall volume of the SRF("% X by vol"). Unless stated otherwise the percent dosage % will, by default, always refer to a % by weight to the total measured SRF. Unless stated otherwise, weights are given in grams ("g") or milligrams ("mg"), molecular weight in kilo-Daltons ("kDa"), volume in microliters ("µL") or milliliters ("mL"), and viscosity units are expressed as inherent viscosity (i.e., the ratio of the natural logarithm of the relative viscosity to the mass concentration of the substance, such as a polymer. The unit of inherent viscosity is deciliters per gram (dL/g). A different measure of viscosity is intrinsic viscosity, which is a measure of a solute's contribution to the total viscosity. Another viscosity is dynamic viscosity or absolute viscosity, the units of which are centimeter-gram-seconds, also known as centipoise (cP).

The SRF may comprise 0.1-60% of a polymer composition, or more preferable 30-50% of a polymer composition. The SRF may comprise 0-80% solvent. The drug to polymer weight ratio of the SRF may be 1:100, 1:50, 1:25, 1:20, 1:10, 1:5, 1:2, 1:1, 2:1, or 5:1. The SRF, once located at the target tissue, may release 1-10%, or 11-50% of the drug load in less than 24 hours, 24-72 hours, 3-7 days, 1-4 weeks, 1-3 months or more than 3 months. The SRF may release 80-100% in 24-72 h, 3-7 days, 1-4 weeks, 1-3 months or more than 3 months.

The drug carrier may be a polymer composition including silk-elastin like protein polymers, Pluronics F68 or F127 or a combination thereof, poly(ε-caprolactone) (PC), polylactides (PLA), poly(D,L-lactide) (PDLA), poly(ortho esters), polyanhydrides, polycarbonates, polyethylene glycol (PEG), polyethylene oxide (PEO), polyesteramides, and any combinations thereof including block and random co-polymers such as but not limited to poly(lactide-co-glycolide) (PLGA) and PLGA-PEG-PLGA. More specifically the PLGA composition may consist of poly(D,L-lactide-co-glycolide) (50:50), poly(D-lactide-co-glycolide) (50:50), poly(L-lactide-co-glycolide) (50:50), poly(D,L-lactide-co-glycolide) (65:35), poly(D-lactide-co-glycolide) (65:35), poly(L-lactide-co-glycolide) (65:35), poly(D,L-lactide-co-glycolide) (75:25), poly(D-lactide-co-glycolide) (75:25), poly(L-lactide-co-glycolide) (75:25), poly(D,L-lactide-co-glycolide) (85:15) or a mixture thereof. The PLGA may be end-capped with ester, acid, alcohol, thiol or other end-groups. The inherent viscosity of the PLGA polymer may vary from 0.1 dL/g to greater than 1.0 dL/g. The molecular weight of the PLGA polymer may vary from 10 kDa up to 150 kDa. The polymer may be linear, branched, hyperbranched, dendritic, have a star structure, or be a dendrimer-like star polymer.

Additional embodiments of the drug carrier, SRF and composition follow.

The drug carrier may include a polymer composition including poly(lactide-co-glycolide), poly(D,L-lactide-co-glycolide), poly(D,L-lactide), ester end capped poly(D,L-lactide-co-glycolide) (50-50), ester end capped poly(D,L-lactide-co-glycolide) (65-35), ester end capped poly(D,L-lactide-co-glycolide (75-25), ester end capped poly(D,L-lactide-co-glycolide (85-15), acid end capped poly(D,L-lactide-co-glycolide) (50-50), acid end capped poly(D,L-lactide-co-glycolide) (65-35), acid end capped poly(D,L-lactide-co-glycolide (75-25), acid end capped poly(D,L-lactide-co-glycolide (85-15), ester end capped poly(D-lactide-co-glycolide) (50-50), ester end capped poly(D-lactide-co-glycolide) (65-35), ester end capped poly(D-lactide-co-glycolide (75-25), acid end capped poly(D-lactide-co-glycolide) (50-50), acid end capped poly(D-lactide-co-glycolide) (65-35), acid end capped poly(D-lactide-co-glycolide (75-25), ester end capped poly(L-lactide-co-glycolide) (50-50), ester end capped poly(L-lactide-co-glycolide) (65-35), ester end capped poly(L-lactide-co-glycolide (75-25), acid end capped poly(L-lactide-co-glycolide) (50-50), acid end capped poly(L-lactide-co-glycolide) (65-35), acid end capped poly(L-lactide-co-glycolide (75-25), ester end capped poly(D,L-lactide-co-glycolide), acid end capped poly(D,L-lactide-co-glycolide), or combinations thereof.

In some embodiments the drug carrier may include a bioabsorbable polymer composition and the inherent viscosity of the polymer composition is between 0.1-1.0 dL/g, 0.1-0.6 dL/g, or 0.1 to 0.4 dL/g or 0.1 to 0.3 dL/g and the ratio of DL-lactide to glycolisfr#de is from 30/70 up to 90/10, 95/5, or 85/15.

In some embodiments the composition may include a bioabsorbable polymer at a concentration of 20-80%, 25-75%, 40-60% by wt. of the bioabsorbable polymer composition, 80-20%, 75-25%, 60-40%, by wt. of the solvent and 0.5%-30% by wt. drug; 1%-20% by wt. of drug, or 1%-10% by wt. of drug.

The drug carrier (polymer composition) may generally be in the form of amorphous or semi-crystalline, homogenous, or phase-separated, and provided in the form of a liquid solution or, suspension, or as nanoparticles, microspheres or microparticles processed by spray drying, emulsion, electrospray, or extrusion. The biodegradable polymer composition is preferably chosen to substantially biodegrade in a period of about 1 to 3 months, 3 to 6 months or 6 to 12 months.

In some embodiments it may be desirable to formulate the SRF so that the drug carrier is fully biodegraded before the next treatment, e.g., 3 months, 6 months or 12 months after the prior treatment. For example, the polymer would have a ratio of glycolide to lactide of 70:30 up to 15:85 for a less hydrophobic structure (faster degradation) and/or an inherent viscosity less than about 1.0 dL/g or more preferably less than 0.3 dL/g.

A polymer composition, when forming a constituent of the SRF, is a polymer composition that enables or achieves a desired "sustained release" of the one or more drugs to the target tissue. In some embodiments, the polymer composition enables or achieves at least 50%, or up to about 100%, or substantially all drug release between 30 and 90 days, through a combination of diffusion and degradation. In other embodiments up 100% of drug release occurs from 90 to 120 days from treatment. Preferably, there is an initial burst (e.g., up to 50% of drug) followed by a substantially reduced rate of release over the next following month, or several following months following treatment. For example, the drug has a release rate of between 5% to 50% during the first 24 hours from injecting the composition into the prostate and the drug has a release rate of no more than 10% to 75% over the first month, 25% to 95% over the first three months, and/or 50% to 100% over the first six months.

As discussed earlier, the SRF has to keep drug exposure to the prostate and minimize leak or flow to other surrounding organs. In addition, the SRF should not take up too much volume in the prostate. A desired shape of the drug release curve could be a burst of drug and early tissue exposure for fast efficacy and then reduced rate of drug release over a 3-6 month period for sustained efficacy. In some examples the drug release curve could be a burst of drug and early tissue exposure for fast efficacy and then reduced rate of drug release over a 1-4 month period for sustained efficacy. For example, a fast burst release rate followed by a reduced rate was achieved with N-methyl pyrrolidone (NMP) solvent that is water soluble. This formulation can provide a high release within the first 24 or 48 hours, or within the first 1 week, two weeks, or up to 3 months, followed by a reduced rate of release.

FIG. 1 shows a Drug Release Curve for Sustained Release Formulation (SRFs) A, B and C. These exemplary SRFs provide a burst followed by gradual release of drug over a period of up to 6 months. SRF A releases about 25% of the drug within the first month, followed by a slow, gradual release where about 95% is released at six months. SRF B has an initial burst of about 50% within the first month, followed by about 100% release at two months. SRF C has an initial burst of about 75% within the first month, with about 100% release at about two months.

TABLE 4A below shows examples of SRF formulations for each of SRF A, B and C. Examples A1, A2 exhibit approximately the same release rate characteristics as SRF A in FIG. 1. Examples B1, B2 exhibit approximately the same release rate characteristics as SRF B in FIG. 1. Examples C1, C2 exhibit approximately the same release rate characteristics as SRF C in FIG. 1. TABLE 4B shows examples of drug released over time.

TABLE 4A

Species of SRF formulations for SRF A, B and C in FIG. 1

| SRF | polymer | drug | % vol. drug v. polymer | Solvent |
|---|---|---|---|---|
| A1 | PLGA8515 | Sirolimus | 1-2% drug, 50% polymer | NMP |
| A2 | PLGA8515 | Paclitaxel | 1-2% drug, 50% polymer | NMP |
| B1 | PLGA7525 | Sirolimus | 3-5% drug, 45-47% polymer | NMP |
| B2 | PLGA7525 | Paclitaxel | 3-5% drug, 45-47% polymer | NMP |
| C1 | PLGA5050 | Sirolimus | 1-5% drug, 45-55% polymer | NMP |
| C2 | PLGA5050 | Paclitaxel | 1-5% drug, 45-55% polymer | NMP |

TABLE 4B plotted ranges for SRF A, B & C (FIG. 1)

| Time (months) | SRF A (drug release %) | SRF B (drug release %) | SRF C (drug release %) |
|---|---|---|---|
| 0 | 0 | 0 | 0 |
| 0.5 | 30 ± 20 | 50 ± 25 | 75 ± 25 |
| 1 | 50 ± 20 | 75 ± 15 | 95 ± 5 |
| 2 | 60 ± 15 | 95 ± 5 | 100 |
| 3 | 70 ± 10 | 100 | |
| 6 | 95 ± 5 | | |

The SRF is delivered to the target tissue in the form of a composition in liquid form (i.e., the SRF's drug(s) and drug carrier are in solution, or in suspension in a solvent when in the delivery vehicle) that gels upon contact with water at the target tissue. The SRF may be made by dissolving the SRF components in a suitable solvent. Suitable solvents for these embodiments include water, N-methylpyrrolidone (NMP), dimethyl sulfoxide (DMSO), 2-pyrrolidone, propylene carbonate, caprolactam, triacetin, alcohols, benzyl benzoate, ethyl acetate, triethyl citrate, benzyl alcohol, glyme (dimethoxyethane), diglyme, and other glycol ethers, and dichloromethane, or any mixture thereof.

As explained earlier, the composition should be formulated at a concentration and viscosity that permits passage through a long, narrow needle having a slenderness ratio within the prescribed ranges deliverable in low unit volumes, and controls the drug release, and drug distribution. Drug to polymer ratios, which influence the viscosity of the composition, may vary from 0.025 to 2.0. Drug and polymer concentrations in solvent may range from 0.1 wt % up to 60 wt % or more preferably 30 wt % to 50 wt %. Unit volumes may range from 0.025 mL up to 0.15 mL per injection or more preferably from 0.05 mL to 0.10 mL per injection. Total volume of the composition for a treatment may range from 0.050 mL up to 1.5 mL or more preferably 0.10 mL to 1.0 mL. Overall dosage of drug provided in the SRF can range from 50 ug up to 200 mg or more preferably from 5 mg to 50 mg. For example, a composition containing the SRF is 300 ug of sirolimus or paclitaxel dissolved with 3000 ug ("ug"-micrograms) poly (D, L-lactide-co-glycolide) (85:15) in NMP at a 50 wt % concentration.

The following disclosure provides further, non-limiting examples for treating prostatic hyperplasia tissues within a patient using an apparatus or medical device according to the disclosure and provides a description of, and results from the second pre-clinical study referred to earlier.

As discussed above, the local drug delivery device is a syringe needle for delivery of the composition including the SRF to the target tissue, as earlier shown and described with reference to FIGS. 2A and 2B. In other embodiments, the applicator portion of a delivery vehicle may include syringe chambers for holding the drug and drug carrier separate from each other, a mixing element for combining the drug and drug carrier such as a static mixing Y-adapter that feeds into a narrow and long, or high slenderness ratio needle. Alternatively, the drug and drug carrier may be mixed using two syringes connected with an adapter, with back and forth plunging to mix the drug and drug carrier. The syringe needle may be imaged under ultrasound to visualize the therapy. Echogenicity may be enhanced by dimpling of the applicator needle or coatings. Echogenicity may also be enhanced by incorporation of contrast enhancing agents such as microbubbles, sulfur hexafluoride, octofluoropropane, air, lipid and/or albumin shells. The applicator may have components for attachment to a rectal ultrasound probe. The applicator may have markings demonstrating measurement of lengths of needle insertion or composition volume. The applicator may have a user-friendly handle and plunger to comfortably deliver the needle to the target tissue. An applicator needle size may range from 16 G up to 25 G. The needle length may range from 10 cm to 30 cm (e.g., 15 cm, 20 cm length) in order to reach the target tissue from a transrectal or transperineal approach.

EXAMPLE

A preclinical canine study was conducted to evaluate the safety and feasibility of a composition comprising an SRF (SRF1) injected into the prostates of six canines, each having enlarged prostates post weekly treatments by testosterone injection over a period of 12 weeks. The SRF1 treatment was delivered 12 weeks post the initial testosterone injections. The composition comprising SRF1 was delivered to these BPH canine models in the following manner:

SRF1 with PLGA 5050 and NMP included 5 mg paclitaxel delivered to a BPH canine model prostate (N=4) in a 100 microliter composition by injecting two 50 microliter injections of the composition into each side or lobe of the prostate while imaging by transrectal ultrasound guidance using a 20 G×20 cm Chiba needle delivered via a 250 microliter gastight glass delivery syringe. The composition was easy for the user to deliver and visualize under ultrasound without discomfort to the animal. A total of 2 injections (50 microliter each) were made to each BPH canine model to deliver SRF1.

10 mg paclitaxel was delivered to the BPH canine model prostate (N=2) in a 200 microliter (ul) composition by injecting two 100 uL of the composition into each side or lobe of the prostate while imaging by transrectal ultrasound guidance using a 20 G×20 cm Chiba needle delivered via 500 microliter gastight glass delivery syringe. The composition was readily observable by the user to deliver and visualize under ultrasound and did not cause any discomfort to the animal. A total of 2 injections (100 microliter each) were made to each BPH canine model to deliver SRF1.

Blood samples were collected from all animals at 0, 1, 3, 7, 14, 30, 60 and 90 days post treatment or until the animal was euthanized. 30 and 90 days following the procedure the models were humanely euthanized and evaluated to determine whether there were any acute, toxic effects of the injectate. At the time the animals were euthanized tissue samples were also collected from the prostate, bladder, and urethra to determine the residual drug concentrations. The day-to-day behavior of all animals was also studied over the 30-and-90 days periods following the procedure.

Data collected from each of the models (i.e., the 30- and 90-day studies):
Prostate Morphology and Prostate Size/Weight Baseline and Post-Treatment (Ultrasound)
Gross Necropsy and Camera/Microscope Imaging at Termination, Fixation
Histology Imaging at Treatment Site at Termination (H&E)

TABLE 5 shows prostate volume (cc, or cm 3) as measured by ultrasound at baseline (i.e., before the animal received SRF1) and 4 weeks and 12 weeks post SRF1 treatment. TABLE 5 shows a reduction in prostate volume (%) post SRF1 treatment relative to baseline.

TABLE 5

| Animal# | Drug Dose (mg) | Prostate Volume by Ultrasound (cm³ or cc) | | | Reduction from Baseline in Prostate Volume (%) | |
|---|---|---|---|---|---|---|
| | | Baseline | 4 weeks post SRF1 | 12 weeks post SRF1 | 4 weeks post SRF1 | 12 weeks post SRF1 |
| 50 | 5 | 39.2 | 10.6 | — | −72.9 | — |
| 45 | 5 | 26.4 | 7.54 | — | −71.4 | — |
| 42 | 10 | 29.7 | 5.87 | — | −80.3 | — |
| 46 | 5 | 19.5 | — | 13.7 | — | −29.9 |
| 52 | 5 | 22.2 | — | 8.65 | — | −61.0 |
| 44 | 10 | 44.1 | — | 8.77 | — | −80.1 |

The BPH canine models in the study are distinguished by number. Animal numbers 45, 46, 50, and 52 received the 5 mg drug dose of SRF1. BPH canine animal numbers 42 and 44 received the 10 mg drug dose. Prostate volumes decreased by as much as 80% 4 weeks and twelve weeks from treatment (animal 44). For example, the prostate volume for animal 50 reduced by 72.9% ([(10.6/39.2)−1]*100=−72.9%).

TABLE 6

| Dose (mg) | Prostate Volume by Ultrasound (cc, Mean) | | % Prostate Volume Reduction (Mean) | |
|---|---|---|---|---|
| | 4 weeks post SRF1 | 12 weeks post SRF1 | 4 weeks post SRF1 | 12 weeks post SRF1 |
| 5 | 9.09 | 11.2 | −72.1 | −45.5 |
| 10 | 5.87 | 8.77 | −80.3 | −80.1 |

TABLE 6 shows the mean average change in canine prostate volume (cc) as

TABLE 7

| Tissue | Overall (n = 3) 30-day (ug/g) | | 5 mg dose (n = 2) 30-day (ug/g) | | 10 mg dose (n = 1) 30-day (ug/g) | |
|---|---|---|---|---|---|---|
| | Mean | Standard Deviation | Mean | Standard Deviation | Mean | Standard Deviation |
| Main Bladder | 0.16 | 0.14 | 0.10 | 0.12 | 0.29 | NA |
| Bladder neck | 0.05 | 0.06 | 0.02 | 0.02 | 0.12 | NA |
| Adventitia/Adipose Tissue | 1.20 | 2.05 | 1.80 | 2.51 | 0.02 | NA |
| Prostate tx1 | 16.01 | 6.91 | 20.00 | 0.00 | 8.03 | NA |
| Prostate tx2 | 17.07 | 5.08 | 20.00 | 0.00 | 11.20 | NA |
| Prostate adj 1 | 13.92 | 9.59 | 19.45 | 0.78 | 2.87 | NA |
| Prostate adj2 | 11.15 | 7.37 | 9.17 | 9.23 | 15.10 | NA |

TABLE 7-continued

| | Overall (n = 3) 30-day (ug/g) | | 5 mg dose (n = 2) 30-day (ug/g) | | 10 mg dose (n = 1) 30-day (ug/g) | |
|---|---|---|---|---|---|---|
| Tissue | Mean | Standard Deviation | Mean | Standard Deviation | Mean | Standard Deviation |
| Prostate distal 1 | 6.23 | 9.17 | 9.12 | 10.87 | 0.46 | NA |
| Prostate distal 2 | 1.46 | 1.75 | 2.17 | 1.76 | 0.04 | NA |
| Prostate remains | 9.28 | 10.03 | 13.86 | 8.68 | 0.12 | NA |
| Urethra proximal | 1.10 | 1.82 | 1.60 | 2.26 | 0.10 | NA |
| Urethra distal | 0.06 | 0.05 | 0.03 | 0.03 | 0.11 | NA | a function of the drug dose injected (5 mg and 10 mg) and measured by transrectal ultrasound, post SRF1 injections (4 and 12 weeks) and post SRF1 treatments (4 and 12 weeks).

TABLE 7 shows the overall (N=3) mean and standard deviation of drug concentrations (ug/g) in the various organ and tissue 30 days post SRF1 treatment. TABLE 7 also shows the mean (and standard deviation for 5 mg) of drug concentrations (ug/g) in the various organ and tissue 30 days post SRF1 treatment for the two doses delivered, 5 mg (N=2) and 10 mg (N=1).

TABLE 8

| | Overall (n = 3) 90-day (ug/g) | | 5 mg dose (n = 2) 90-day (ug/g) | | 10 mg dose (n = 1) 90-day (ug/g) | |
|---|---|---|---|---|---|---|
| Tissue | Mean | Standard Deviation | Mean | Standard Deviation | Mean | Standard Deviation |
| Main Bladder | 0.03 | 0.01 | 0.03 | 0.01 | 0.03 | NA |
| Bladder neck | 0.09 | 0.08 | 0.11 | 0.11 | 0.06 | NA |
| Adventitia/Adipose Tissue | 0.51 | 0.24 | 0.43 | 0.27 | 0.69 | NA |
| Prostate tx1 | 103.97 | 179.29 | 155.60 | 219.77 | 0.71 | NA |
| Prostate tx2 | 10.52 | 15.20 | 14.22 | 19.49 | 3.12 | NA |
| Prostate adj1 | 3.71 | 5.32 | 5.46 | 6.19 | 0.22 | NA |
| Prostate adj2 | 4.64 | 6.76 | 6.94 | 7.73 | 0.04 | NA |
| Prostate distal 1 | 4.37 | 3.82 | 2.56 | 3.11 | 7.98 | NA |
| Prostate distal 2 | 1.83 | 2.72 | 2.69 | 3.21 | 0.10 | NA |
| Prostate remains | NA | NA | NA | NA | NA | NA |
| Urethra proximal | 0.51 | 0.53 | 0.22 | 0.22 | 1.10 | NA |
| Urethra distal | 0.29 | 0.35 | 0.39 | 0.43 | 0.08 | NA |

TABLE 8 shows the overall (N=3) mean and standard deviation of drug concentrations (ug/g) in the various organ and tissue 90 days post SRF1 treatment. TABLE 8 also shows the mean (and standard deviation for 5 mg) of drug concentrations (ug/g) in the various organ and tissue 30 days post SRF1 treatment for the two doses delivered, 5 mg (N=2) and 10 mg (N=1).

TABLE 9 summarizes histopathology scoring from histopathology H&E microscopic images post SRF1 injection in each of the canine BPH prostates. Scoring ranges from 0 to 4 (0=none, 1=minimal, 2=mild, 3=moderate and 4=marked/severe/complete). Minimal to moderate values of necrosis and inflammation over time are evident of the localized drug effect of necrosis observed in the histopathology images. Minimal to mild fibrosis that resolves over time from 30 days to 90 days is likely evident of the drug effect in reducing the prostate volume (StDev=Standard Deviation).

It is known that for aging men with a history of BPH and a reduced serum testosterone concentration the size of the prostate is not reduced when serum total testosterone con-

TABLE 9

| Timepoint (days) | Acinar dilation (0-4) | | Eosinophilic Amorphous material (0-4) | | Necrosis (0-4) | | Fibrin (0-4) | | Inflammation (0-4) | | Fibrosis (0-4) | |
|---|---|---|---|---|---|---|---|---|---|---|---|---|
| | Mean | StDev | Mean | StDev | Mean | StDev | Mean | StDev | Mean | StDev | Mean | StDev |
| Overall | | | | | | | | | | | | |
| 30 (n = 3) | 0.68 | 0.79 | 1.53 | 1.40 | 1.27 | 1.21 | 0.27 | 0.12 | 2.20 | 1.25 | 1.07 | 0.46 |
| 90 (n = 3) | 1.00 | 0.00 | 0.80 | 0.80 | 0.47 | 0.42 | 0.00 | 0.00 | 1.20 | 0.87 | 0.33 | 0.58 |
| 5 mg Drug Dose | | | | | | | | | | | | |
| 30 (n = 2) | 0.90 | 0.99 | 1.60 | 1.98 | 1.20 | 1.70 | 0.20 | 0.00 | 2.70 | 1.27 | 0.80 | 0.00 |
| 90 (n = 2) | 1.00 | 0.00 | 1.20 | 0.57 | 0.70 | 0.14 | 0.00 | 0.00 | 1.50 | 0.99 | 0.00 | 0.00 |
| 10 mg Drug Dose | | | | | | | | | | | | |
| 30 (n = 1) | 0.25 | NA | 1.40 | NA | 1.40 | NA | 0.40 | NA | 1.20 | NA | 1.60 | NA |
| 90 (n = 1) | 1.00 | NA | 0.00 | NA | 0.00 | NA | 0.00 | NA | 0.60 | NA | 1.00 | NA | centration is reduced. See Xia, B.-W. et al, *Relationship between serum total testosterone and prostate volume in aging men*, Scientific Reports, 11, 14122 (2021).

As mentioned earlier, while prior methods may show efficacy in reducing BPH, they either may require a more invasive procedure (vs. localized treatment using the delivery device as disclosed herein, such as the needle used in the animal study), more frequent treatment due to diffusion or more generalized treatment of BPH raising the possibility of adverse effects because a higher dosage is needed to treat the area while accounting for leakage or diffusion of the drug to other areas. Adverse effects may include diminished urinary or sexual function. It is desired to have an effective treatment targeting only the target tissue and nowhere else (e.g., avoiding the urethra) and to perform the procedure in a less invasive manner for patient acceptance.

As mentioned earlier, both injection volumes of SRF1 showed significant reduction in prostate size, as reported in TABLES 5 and 6. Additionally, as shown in FIGS. 7 and 8, there was very low systemic drug concentrations present in the blood, indicating that the agent was contained at the target tissue. The Example (pre-clinical study 2) indicates that an effective SRF injectate according to the disclosure (1) reduces prostate volume significantly over a 30 and 90 day period, (2) limits substantially all of the active agent to the target tissue, and (3) is capable of being delivered as a series of low unit volumes using a needle syringe. As for point (2), it should be mentioned that other known products for treating BPH by contrast have their active agents disperse significantly (systemic drug concentrations much higher than what is shown in FIGS. 7-8). Moreover, the study indicated a significant ratio of prostate 30-day drug concentration to maximum plasma drug concentration of at least about 10,000. As mentioned throughout, it is important to control diffusion of the agent as this can cause adverse effects on nearby tissue and organs. Additionally, in contrast to most prior or existing techniques for treating BPH, a comparatively small volume of SRF injectate is needed for efficacy. In the example (pre-clinical study) a unit volume of the composition comprising SRF1 was between 10-200 microliter per injection over 1-10 injections across each side of the prostate, or 50-100 microliter per injection over 1-5 injections across each side of the prostate. Prior approaches for treating BPH seek to maximize injection volumes for increased drug dosage. An SRF however does not require as high a drug dosage, because the drug is maintained in the target tissue.

Following are additional listing of disclosed embodiments:

0.5 mL N-methyl pyrrolidone (NMP) was added to a vial with 0.25 g sirolimus and vortexed until dissolved. 50 microliter of drug solution was added to 2.5 mL of a 50% PLGA8515A (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 50 microliter of drug solution was added to 2.5 mL of a 50% PLGA8515A (0.5 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 50 microliter of drug solution was added to 2.5 mL of a 50% PLGA8515E (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 50 microliter of drug solution was added to 2.5 mL of a 50% PLGA8515E (0.5 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 50 microliter of drug solution was added to 2.5 mL of a 50% PLGA8515A (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 50 microliter of drug solution was added to 2.5 mL of a 50% PLGA8515E (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA8515A (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA8515E (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA8515A (0.5 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA8515E (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA8515E (0.3 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA8515A (0.5 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA8515E (0.7 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 200 microliter of drug solution was added to 2.5 mL of a 50% PLGA8515 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 50 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 200 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g sirolimus and vortexed until dissolved. 50 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 200 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515A (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515E (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515A (0.5 dl/g) in NMP solution using syringe to syringe mixing with a female to female luer connector. 250 microliters in a 1 mL syringe was loaded into a 20 G×20 cm Chiba biopsy needle with depth markers. 0.5 mL N-methyl pyrrolidone (NMP) was added to a vial with 0.25 g everolimus and vortexed until dissolved. 50 microliter of drug solution was added to 2.5 mL of a 50% PLGA8515E (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515A (0.5 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515E (0.7 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515E (0.5 dl/g) in NMP solution using syringe to syringe mixing with a female to female luer connector. 800 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515A (0.7 dl/g) in NMP solution using syringe to syringe mixing with a female to female luer connector. 800 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515A (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515E (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 100 microliter of drug solution was added to 2.5 mL of a 50% PLGA8515 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 200 microliter of drug solution was added to 2.5 mL of a 50% PLGA8515 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 100 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 200 microliter of drug solution was added to 2.5 mL of a 50% PLGA7525A (0.3 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA7525E (0.3 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA7525A (0.5 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA7525E (0.5 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA7525A (0.7 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA7525E (0.7 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA6535E (0.3 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA6535A (0.3 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA6535E (0.5 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA6535A (0.5 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA6535E (0.5 dl/g) in NMP solution using syringe to syringe mixing with a female to female luer connector. 500 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA6535A (0.5 dl/g) in NMP solution using syringe to syringe mixing with a female to female luer connector. 500 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 50 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 100 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 200 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 50 microliter of drug solution was added to 2.5 mL of a 50% PLGA8515 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515A (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515E (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515A (0.5 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515E (0.5 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515A (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515E (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515A (0.5 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515E (0.5 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515A (0.7 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 500 microliter of drug solution was added to 2.5 mL of a 50% PLGA8515E (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 200 microliter of drug solution was added to 2.5 mL of a 50% PLGA8515 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 50 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 200 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g paclitaxel and vortexed until dissolved. 100 microliter of drug solution was added to 2.5 mL of a 50% PLGA6535A (0.3 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA6535A (0.5 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 500 microliter of drug solution was added to 2.5 mL of a 50% PLGA6535E (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 500 microliter of drug solution was added to 2.5 mL of a 50% PLGA6535E (0.5 dl/g) in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.25 g paclitaxel and vortexed until dissolved. 400 mg of drug solution was added to 2.9 g of a 20% by weight PLGA5050A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 30% by weight PLGA5050A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 40% by weight PLGA5050A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 40% by weight PLGA5050A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 50% by weight PLGA5050A in NMP solution using syringe to syringe mixing with a female to female luer connector (#SRF1). 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 50% by weight PLGA5050A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.25 g paclitaxel and vortexed until dissolved. 400 mg of drug solution was added to 2.9 g of a 20% by weight PLGA5050E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 30% by weight PLGA5050E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 40% by weight PLGA5050E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 40% by weight PLGA5050E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 50% by weight PLGA5050E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 50% by weight PLGA5050E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.25 g paclitaxel and vortexed until dissolved. 400 mg of drug solution was added to 2.9 g of a 20% by weight PLGA8515A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 30% by weight PLGA8515A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 40% by weight PLGA8515A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 40% by weight PLGA8515A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 50% by weight PLGA8515A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 50% by weight PLGA8515A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.25 g paclitaxel and vortexed until dissolved. 400 mg of drug solution was added to 2.9 g of a 20% by weight PLGA8515E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 30% by weight PLGA8515E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 40% by weight PLGA8515E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 40% by weight PLGA8515E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 50% by weight PLGA8515E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 50% by weight PLGA8515E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.25 g paclitaxel and vortexed until dissolved. 400 mg of drug solution was added to 2.9 g of a 20% by weight PLGA6535A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 30% by weight PLGA6535A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 40% by weight PLGA6535A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 40% by weight PLGA6535A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 50% by weight PLGA5050A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 50% by weight PLGA6535A in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.25 g paclitaxel and vortexed until dissolved. 400 mg of drug solution was added to 2.9 g of a 20% by weight PLGA6535E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 30% by weight PLGA6535E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 40% by weight PLGA6535E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 40% by weight PLGA6535E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 50% by weight PLGA6535E in NMP solution using syringe to syringe mixing with a female to female luer connector. 250 microliters in a 1 mL syringe was loaded into a 20 G×20 cm Chiba biopsy needle with depth markers.

1.08 g N-methyl pyrrolidone (NMP) was added to a vial with 0.50 g paclitaxel and vortexed until dissolved. 400 mg of drug solution was added to 2.9 g of a 50% by weight PLGA6535E in NMP solution using syringe to syringe mixing with a female to female luer connector. 250 microliters in a 1 mL syringe was loaded into a 20 G×20 cm Chiba biopsy needle with depth markers.

Additional aspects of the disclosure are set forth in the Embodiments E1-E48:

E1. A Sustained Release Formulation (SRF) for treating BPH by dispensing no more than a unit volume of the SRF at a location in the prostate using a needle syringe, comprising: a cytostatic or cytotoxic drug; a glycolide-based bioabsorbable copolymer; and a water soluble solvent capable of dissolving the drug and copolymer.

E2. The SRF of E1 or any embodiments depending from E1, wherein the glycolide-based bioabsorbable copolymer is selected from the set of poly(D,L-lactide-co-glycolide) (50:50), poly(D,L-lactide-co-glycolide) (65:35), and poly(D,L-lactide-co-glycolide) (85:15).

E3. The SRF of E1 or any embodiments depending from E1, wherein the water soluble solvent capable of dissolving the drug and copolymer is selected from the set of N-methylpyrrolidone (NMP) and dimethyl sulfoxide (DMSO).

E4. The SRF of E1 or any embodiments depending from E1, wherein the cytotoxic drug is selected from the set of paclitaxel, docetaxel, taxanes, protaxel, vincristine, etoposide, nocodazole, indirubin, anthracycline derivatives, daunorubicin, daunomycin, plicamyci, tauromustine, bofumustane, and plicamycin, irinotecan and doxorubicin and combinations thereof.

E6. The SRF of E1 or any embodiments depending from E1, wherein the glycolide-based bioabsorbable copolymer is selected from the set of poly(D,L-lactide-co-glycolide) (PLGA) and PLGA-PEG-PLGA.

E7. The SRF of E1 or any embodiments depending from E1, wherein glycolide-based bioabsorbable copolymer has a total concentration of 25-75% by wt., the solvent has a total concentration of 75-25% by wt., and the cytotoxic or cytostatic drug has a total concentration of 0.5%-30% by wt.; 1%-20% by wt. o, or 2%-6% by wt.

E8. The SRF of E1 or any embodiments depending from E1, wherein the composition is adapted to fully release the drug into the prostate over at least 14 days from being injected into the prostate, or over a 30 to 90 day period, or over a 90 to 180 day period.

E9. The SRF of E1 or any embodiments depending from E1, wherein the drug has a release rate of no more than 10% to 85% over the first month, 25% to 95% over the first three months, and/or 50% to 100% over the first six months.

E10. The SRF of E1 or any embodiments depending from E1, wherein the drug has a release rate of between 5% to 50% during the first 24 hours from injecting the composition into the prostate.

E11. The SRF of E1 or any embodiments depending from E1, wherein the glycolide-based bioabsorbable copolymer has a viscosity of between 0.2-0.5 dL/g, or 0.2 to 0.4 dL/g or 0.2 to 0.3 dL/g and the ratio of DL-lactide to glycolide is from 50/50 up to 85/15.

E12. The SRF of E1 or any embodiments depending from E1, wherein the cytostatic or cytotoxic drug is 0.1 up to 10% wt., 1-15% or up 20-30% wt. of the composition.

E13. The SRF of E1 or any embodiments depending from E1, wherein the solvent comprises N-methyl-pyrrolidone, the drug is paclitaxel and the polymer is PLGA.

E14. The SRF of E1 or any embodiments depending from E1, wherein the SRF is adapted to release the drug into the prostate over at least 14 days from being injected into the prostate, or over a 30 to 90 day period, or over a 90 to 180 day period.

E15. The SRF of E1 or any embodiments depending from E1, wherein the drug is a cytostatic drug consisting of rapamycin, sirolimus, everolimus, temsirolimus, or zotarolimus.

E16. The SRF of E1 or any embodiments depending from E1, where the drug is a cytotoxic drug comprising paclitaxel or docetaxel.

E17. The SRF of E1 or any embodiments depending from E1, wherein the SRF forms into a solid material with shapes of one or more of, or any of combination of microparticles, nanoparticles, rods, or a gel when the SRF comes into contact with the prostate.

E18. An apparatus for treating a prostate volume, PV, comprising: a composition comprising an SRF having an absolute viscosity, $\mu$, and in an amount of at least one unit volume, v; and a syringe containing the composition in a barrel of the syringe, the syringe including a needle having a length, L, and lumen diameter, D, and adapted for being placed in fluid communication with the composition; wherein the syringe holds at least n of the unit volumes, v, n is related to PV as n=PV/(200*v) and the n unit volumes equal a total volume for treating BPH; and wherein the apparatus has a KIR between 10 and 1000, 10 and 300, or 40 and 400, wherein the KIR is defined as $(p)*(L)^2/(vD)*10^(-6)$.

E19. The apparatus of E18 or any claim depending therefrom, wherein $\mu$ is between 500 cP and 6000 cP.

E20. The apparatus of E18 or any claim depending therefrom, wherein L is between 10 and 20 cm.

E21. The apparatus of E18 or any claim depending therefrom, wherein the barrel has a slenderness ratio of between 5 and 50, or more narrowly between 10 and 30.

E22. The apparatus of E18 or any claim depending therefrom, wherein the needle has a slenderness ratio (L/D) of between 200 and 400, or between 250 and 350.

E23. The apparatus of E18 or any claim depending therefrom, wherein the needle has an inner diameter of 0.02 cm to about 0.12 cm or more narrowly 0.06 cm to 0.08 cm.

E24. The apparatus of E18 or any claim depending therefrom, wherein v is between 0.05 ml and 0.2 ml.

E25. The apparatus of E18 or any claim depending therefrom, wherein L is between 15 and 20 cm, the barrel has a slenderness ratio of about 10 and 30, the needle has an inner diameter of 0.06 cm to about 0.08 cm, v is between 0.05 ml and 0.2 ml, and the viscosity is between 1065 cP and 4000 cP.

E26. The apparatus of E18 or any claim depending therefrom, wherein the syringe barrel contains between 2 and 10 unit volumes of the composition, excluding dead volume of composition within the syringe barrel.

E27. The apparatus of E18 or any claim depending therefrom, wherein the composition comprises a bioabsorbable polymer at a total concentration of 40-50% by wt., a solvent at a total concentration of 80-20%, 75-25%, 60-40%, by wt., and a drug at a total concentration of 0.5%-30% by wt.; 1%-20% by wt. o, or 2%-6% by wt.

E28. The apparatus of E18 or any claim depending therefrom, wherein a drug of the SRF has a release rate of no more than 10% to 85% over the first month, 25% to 95% over the first three months, and/or 50% to 100% over the first six months.

E29. The apparatus of E18 or any claim depending therefrom, wherein the drug has a release rate of between 5% to 50% during the first 24 hours from injecting the composition into the prostate.

E30. The apparatus of E18 or any claim depending therefrom, wherein the SRF comprises a cytostatic or cytotoxic drug of 0.1 up to 10% wt., 10-15% or up to 20-30% wt. of the SRF.

E31. The apparatus of E18 or any claim depending therefrom, wherein the drug is sirolimus, docetaxel, or paclitaxel.

E32. The apparatus of E18 or any claim depending therefrom, wherein the drug comprises an alpha blocker or 5-alpha reductase inhibitor, anti-inflammatory such as corticosteroids, and/or vasodilators.

E33. The apparatus of E18 or any claim depending therefrom, wherein the solvent comprises N-methyl-pyrrolidone, the drug is paclitaxel and the polymer is PLGA.

E34. The apparatus of E18 or any claim depending therefrom, wherein the KIR is between 40 and 400.

E35. An apparatus for treating a prostate volume, PV, comprising a composition comprising an SRF having an absolute viscosity, $\mu$, and in an amount of at least one unit volume, v; a syringe containing the composition in a barrel of the syringe, the syringe including a needle having a length, L, and lumen diameter, D, and adapted for being placed in fluid communication with the composition; and wherein the syringe holds at least n of the unit volumes and n is related to PV as n=PV/(200*v); and wherein L is between 15 and 20 cm, the barrel has a slenderness ratio of about 10 and 30, the needle has an inner diameter of 0.06 cm to about 0.08 cm, v is between 0.05 ml and 0.1 ml, and μ is between 1065 cP and 4000 cP; and wherein the apparatus has a KIR between 10 and 1000, defined as $(\mu)*(L)^2/(vD)*10^{(-6)}$.

E36. The apparatus claim 18, wherein the KIR is between 40 and 400.

E37. The apparatus claim 18, wherein the syringe barrel contains between 2 and 10 unit volumes of the composition, excluding dead volume of composition within the syringe barrel.

E38. Method of making, comprising: combining a cytotoxic or cytostatic drug, a glycolide-based bioabsorbable copolymer, and a water soluble solvent capable of dissolving the drug and copolymer to form composition for treating BPH;

E39. The method of making according to E48 or any claim depending therefrom, wherein the composition when placed within a needle syringe forms an apparatus having a KIR of between 10 and 1000.

E.40. The method of making according to E48 or any claim depending therefrom, wherein the composition when delivered to a prostate produces an efficacious outcome when delivered to a prostate as a total volume.

E.41. The method of making according to E48 or any claim depending therefrom, wherein the cytotoxic or cytostatic drug, the glycolide-based bioabsorbable copolymer, and the water soluble solvent are combined when placed within a barrel of the needle syringe.

The invention claimed is:

1. An apparatus comprising:
a needle syringe containing a composition comprising:
  a cytotoxic or cytostatic drug,
  a bioabsorbable copolymer, and
  a water soluble solvent capable of dissolving the drug and copolymer;
wherein
the composition has an absolute viscosity, μ;
the needle syringe has a needle length L with an inner diameter D; and
the needle syringe comprises a plurality, n, of unit volumes of the composition;
a unit volume, v, is from 0.05 ml to 0.2 ml;
the plurality of unit volumes is equal to a total volume for treating Benign Prostatic Hyperplasia (BPH);
the apparatus has a K-injectable rating (KIR) of between 10 to 300 or 40 to 400; and
KIR is defined as $$KIR = \frac{\mu L^2}{vD}(10^{-6}).$$

2. The apparatus of claim 1, wherein the cytotoxic drug is docetaxel or paclitaxel.

3. The apparatus of claim 1, wherein the cytostatic drug is sirolimus.

4. The apparatus of claim 1, wherein the composition has between 4% to 15% by volume of the cytotoxic or cytostatic drug, wherein the cytotoxic drug is docetaxel or paclitaxel, and wherein the cytostatic drug is sirolimus.

5. The apparatus of claim 1, wherein the plurality is an integer, n, and wherein n is related to a prostate volume, PV, for treatment of BPH as n=PV/(200*v).

6. The apparatus of claim 1, wherein the apparatus is configured to deliver the composition by way of transurethral, transperineal or transrectal administration.

7. The apparatus of claim 1, wherein the composition is echogenic and comprises contrast agent to enhance echogenicity.

8. The apparatus of claim 1, wherein the apparatus has a KIR of between 10 and 300.

9. The apparatus of claim 1, wherein the needle syringe comprises a barrel that holds at least n of the unit volumes, n is an integer from 2 to 10; and wherein:
  n is from 2 to 4 when a prostate size is between 20 grams and 40 grams,
  n is from 2 to 6 when the prostate size is between 40 grams and 60 grams,
  n is from 4 to 8 when the prostate size is between 60 grams and 80 grams, and
  n is from 6 to 10 when the prostate size is 80 grams or more.

10. The apparatus of claim 1, wherein a unit volume is between 0.05 ml to 0.1 ml.

11. The apparatus of claim 1, wherein a unit volume is between 0.1 ml to 0.2 ml.

12. The apparatus of claim 1, wherein the prostate size is a prostate volume or a prostate weight, and wherein the prostate volume or prostate weight is determined by an ultrasonic imaging or a magnetic resonance imaging.

13. The apparatus of claim 1, wherein the composition further comprises an alpha blocker or 5-alpha reductase inhibitor or an anti-inflammatory.

14. The apparatus of claim 12, wherein the anti-inflammatory is selected from the group consisting of corticosteroids, vasodilators, and combinations thereof.

15. The apparatus of claim 1, wherein the bioabsorbable copolymer is selected from the group consisting of poly(ethylene glycol) (PEG), poly(D,L-lactide), poly(D,L-lactide-co-glycolide) wherein the molar ratio of lactide to glycolide is 50:50, poly(D,L-lactide-co-glycolide) wherein the molar ratio of lactide to glycolide is 65:35, poly(D,L-lactide-co-glycolide) wherein the molar ratio of lactide to glycolide is 75:25, and poly(D,L-lactide-co-glycolide) wherein the molar ratio of lactide to glycolide is 85:15.

16. The apparatus of claim 1, wherein the water soluble solvent capable of dissolving the drug and copolymer is selected from the group consisting of N-methylpyrrolidone (NMP), dimethyl sulfoxide (DMSO), and combinations thereof.

17. The apparatus of claim 1, wherein the bioabsorbable copolymer is selected from the group consisting of poly(D,L-lactide-co-glycolide) (PLGA) and PLGA-PEG-PLGA.

18. The apparatus of claim 1, wherein the bioabsorbable copolymer has a total concentration of 30-50% by weight, the solvent has a total concentration of 30-50% by weight, and the cytotoxic or cytostatic drug has a total concentration of 0.5%-30% by weight.

19. The apparatus of claim 18, wherein the cytotoxic or cytostatic drug has a total concentration of 2%-6% by weight.

20. The apparatus of claim 1, wherein the solvent comprises N-methyl-pyrrolidone, the drug is paclitaxel, and the bioabsorbable copolymer is PLGA.

* * * * *